(12) United States Patent
Benson et al.

(10) Patent No.: US 9,315,859 B2
(45) Date of Patent: Apr. 19, 2016

(54) DDAO COMPOUNDS AS FLUORESCENT REFERENCE STANDARDS

(71) Applicant: LIFE TECHNOLOGIES CORPORATION, Carlsbad, CA (US)

(72) Inventors: Scott C. Benson, Alameda, CA (US); Cinna Monighetti, San Ramon, CA (US); Sandy M. Koepf, San Francisco, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 14/071,552

(22) Filed: Nov. 4, 2013

(65) Prior Publication Data

US 2014/0134615 A1    May 15, 2014

Related U.S. Application Data

(63) Continuation of application No. 13/339,340, filed on Dec. 28, 2011, now abandoned.

(60) Provisional application No. 61/428,182, filed on Dec. 29, 2010.

(51) Int. Cl.
| | |
|---|---|
| C12Q 1/68 | (2006.01) |
| C12P 19/34 | (2006.01) |
| C09B 15/00 | (2006.01) |
| C07H 21/02 | (2006.01) |
| C07H 21/04 | (2006.01) |

(52) U.S. Cl.
CPC .............. *C12Q 1/6844* (2013.01); *C09B 15/00* (2013.01); *C12Q 1/6851* (2013.01)

(58) Field of Classification Search
CPC .................................................. C12Q 1/6844
USPC .............. 435/6.1, 91.1, 6.12; 536/23.1, 24.3, 536/26.6
See application file for complete search history.

(56) References Cited

U.S. PATENT DOCUMENTS

| | | | |
|---|---|---|---|
| 4,810,636 | A | 3/1989 | Corey |
| 5,393,615 | A | 2/1995 | Corey et al. |
| 5,928,907 | A | 7/1999 | Woudenberg et al. |
| 7,256,292 | B2 | 8/2007 | Graham et al. |
| 7,985,602 | B2 | 7/2011 | Graham et al. |
| 8,729,267 | B2 | 5/2014 | Graham et al. |
| 2003/0162213 | A1 | 8/2003 | Fuller et al. |
| 2005/0176014 | A1* | 8/2005 | Heindl et al. ............ 435/6 |
| 2010/0227327 | A1 | 9/2010 | Xie et al. |

FOREIGN PATENT DOCUMENTS

| | | |
|---|---|---|
| EP | 0270946 B1 | 5/1992 |
| EP | 0459536 B1 | 9/1996 |
| WO | 03/020734 | 3/2003 |
| WO | 03/025192 | 3/2003 |
| WO | 2004/020603 | 3/2004 |
| WO | 2004/072304 | 8/2004 |
| WO | WO-2006/034036 | 3/2006 |
| WO | WO 2006/034036 | * 3/2006 |
| WO | 2011/031497 | 3/2011 |

OTHER PUBLICATIONS

Altria, Kevin D., "Improved Performance in Capillary Electrophoresis Using Internal Standards", Retrieved from the internet: http://www.chromatographyonline.com/lcgc/data/articlestandard/lcgceurope/362002/30473/article.pdf, Sep. 2002; 1-5.
Hill, R. et al., "Uncoupling of Electron Transport by Anionic Quinonoid Redox Indicator Dyes", *New Phytol.*, vol. 77, 1976; 1-9.
Lee, Linda G. et al., "Seven-Color, Homogeneous Detection of Six PCR Products", *Biotechniques*, vol. 27, No. 2, Informa Healthcare, 1999; 342-349.
PCT/US2005/033174; International Search Report and Written Opinion mailed Dec. 27, 2005.
PCT/US2011/067680; International Search Report and Written Opinion mailed Apr. 27, 2012.
PCT/US2011/067959; International Preliminary Report on Patentability mailed Jul. 2, 2013.
Szollosi, Janos et al., "Application of Fluorescence Resonance Energy Transfer in the Clinical Laboratory: Routine and Research", *Cytometry*, vol. 34, 1998; 159-179.
EP15163156.1, Extended European Search Report mailed on Jul. 1, 2015, 8 Pages.

* cited by examiner

*Primary Examiner* — Jezia Riley
(74) *Attorney, Agent, or Firm* — Thompson Hine LLP

(57) ABSTRACT

According to the present teachings, methods and compositions are provided that utilize at least one reference dye of formula (I):

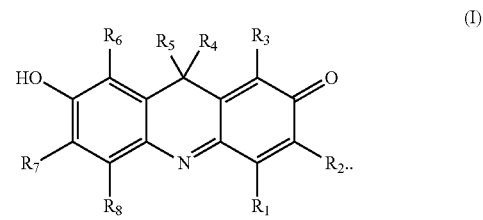

In some embodiments, a method comprises measuring a detection signal of a reporter dye and at least one reference dye of formula (I). In some embodiments, a composition comprises a reference dye of formula (1), a buffer, a selection of nucleotides and a protein.

16 Claims, 17 Drawing Sheets

|    | FAM | VIC | TED | SID |
|----|-----|-----|-----|-----|
| 1  | background | background | background | background |
| 2  | SIGNAL | background | background | background |
| 3  | background | SIGNAL | background | background |
| 4  | background | background | SIGNAL | background |
| 5  | background | background | background | SIGNAL |
| 6  | SIGNAL | SIGNAL | background | background |
| 7  | SIGNAL | background | SIGNAL | background |
| 8  | SIGNAL | background | background | SIGNAL |
| 9  | background | SIGNAL | SIGNAL | background |
| 10 | background | SIGNAL | background | SIGNAL |
| 11 | background | background | SIGNAL | SIGNAL |
| 12 | SIGNAL | SIGNAL | SIGNAL | background |
| 13 | SIGNAL | SIGNAL | background | SIGNAL |
| 14 | background | SIGNAL | SIGNAL | SIGNAL |
| 15 | SIGNAL | background | SIGNAL | SIGNAL |
| 16 | SIGNAL | SIGNAL | SIGNAL | SIGNAL |

FIG. 8

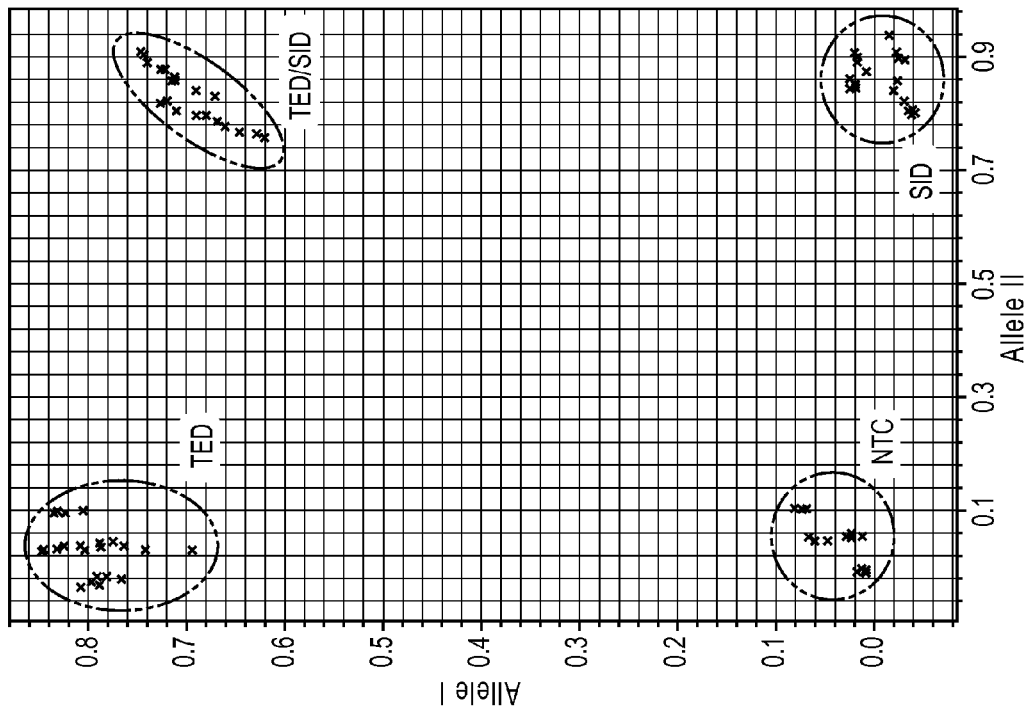
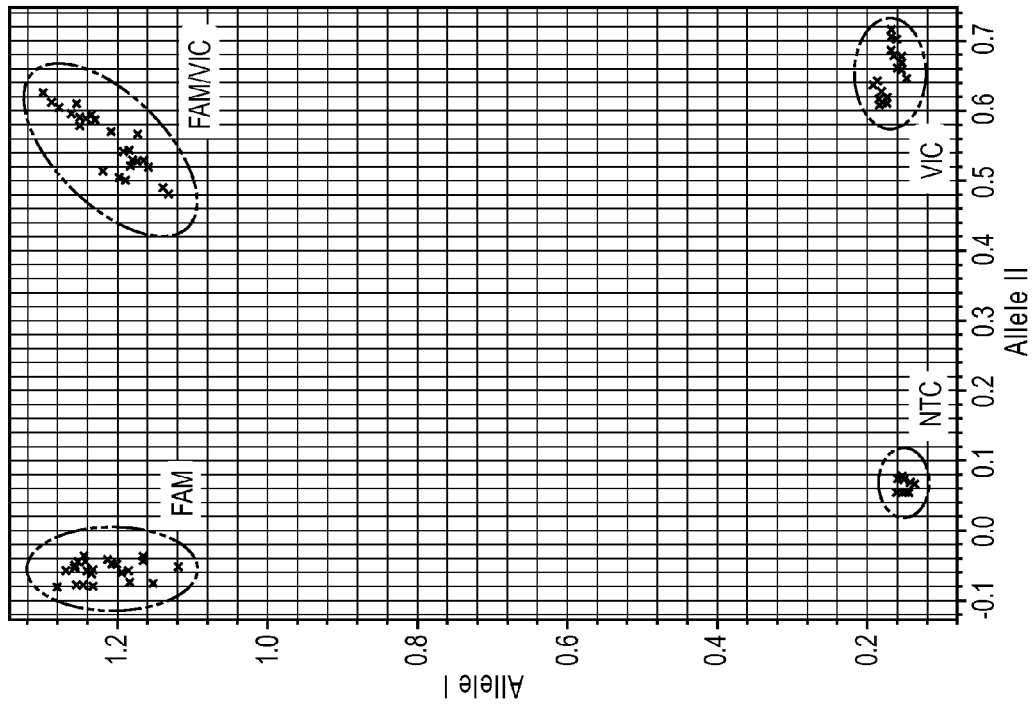

DDAO COMPOUNDS AS FLUORESCENT REFERENCE STANDARDS

CROSS-REFERENCE TO RELATED APPLICATIONS

This application is a continuation application of U.S. application Ser. No. 13/339,340, filed Dec. 28, 2011, now abandoned, which claims priority to U.S. application No. 61/428,182, filed Dec. 29, 2010, which disclosures are herein incorporated by reference in their entirety.

BACKGROUND

A reference dye can be beneficial in many different many assays. Reference dyes can be used for calibration, normalization, and to ensure an assay is being carried out properly. In multiplex reactions, which may contain multiple dyes to identify multiple targets, it can be difficult to find a stable reference dye that emits at a wavelength distinct from the other dyes and does not interfere with the reaction.

SUMMARY

In some embodiments a method is provided, wherein the method may comprise (a) forming a mixture comprising at least one probe and a reference dye, wherein each of the at least one probes comprises a target-specific moiety and a reporter dye, wherein each target-specific moiety is specific for a different target and each reporter dye is different from the others, and wherein the reference dye has formula (I):

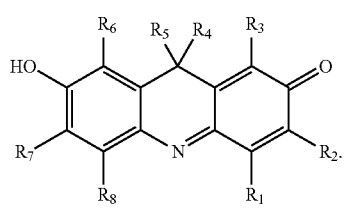

wherein:
each of $R_1$ to $R_3$ and $R_6$ to is independently —H, halogen, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, and substituted $C_1$-$C_6$ alkoxy, wherein R is $C_1$-$C_6$ alkyl, substituted $C_1$-$C_6$ alkyl, $C_1$-$C_6$ alkoxy, and substituted $C_1$-$C_6$ alkoxy;
$R_4$ and $R_5$ taken separately are selected from $C_1$-$C_6$ alkyl, and $C_1$-$C_6$ substituted alkyl, or $R_4$ and $R_5$ taken together are selected from $C_3$-$C_7$ cycloalkyl, $C_4$-$C_7$ unsaturated cycloalkyl, $C_3$-$C_7$ substituted cycloalkyl or $C_4$-$C_7$ substituted unsaturated cycloalkyl; and
(b) measuring fluorescence emitted by the reference dye; (c) measuring fluorescence emitted by and at least one reporter dye. In various embodiments, the method may additionally include adjusting the measured fluorescence emitted by the at least one reporter dye based on the measured fluorescence emitted by the reference dye, to form an adjusted measurement. In some embodiments, the mixture comprises at least two, at least three, at least four, or at least five probes.

In some embodiments, $R_1$ is selected from hydrogen, halogen, methyl, and ethyl; $R_2$ and $R_3$ are each independently a halogen; $R_4$ and $R_5$ are each independently selected from methyl and ethyl; $R_6$ is selected from hydrogen, halogen; methyl, and ethyl; $R_7$ is selected from hydrogen, halogen, methyl, ethyl, and $SO_3H$; and $R_8$ is selected from hydrogen, halogen, methyl; and ethyl. In some embodiments, $R_2$ and $R_3$ are each chlorine and $R_7$ is hydrogen or $SO_3H$. In some embodiments, the reference dye is selected from:

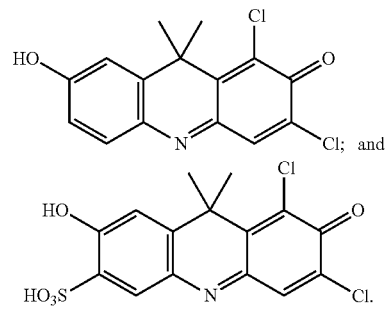

In some embodiments the target-specific moiety may be selected from an oligonucleotide, a peptide, an antibody, an antigen, a small molecule, a metabolite, and a polysaccharide. In some embodiments, the target may be selected from a polynucleotide, an antigen, an antibody, a receptor, an enzyme, an organelle, a membrane, and a cell. In some embodiments, the target-specific moiety may be an oligonucleotide. In some embodiments, the probe comprises an oligonucleotide, a reporter dye, and a quencher dye. In some embodiments, the target may be a polynucleotide. In some embodiments, the method may comprise amplifying at least a portion of the polynucleotide.

In some embodiments, the fluorescence emitted by each reporter dye can be measured in the presence of the other reporter dyes and the reference dye in the mixture. In some embodiments, the fluorescence emitted by the reference dye can be measured in the presence of the reporter dyes in the mixture.

In some embodiments, a method may comprise; irradiating the mixture with a first excitation wavelength range; detecting radiation emitted by at least a first reporter dye; irradiating the mixture with a second excitation wavelength range that differs from the first excitation wavelength range; and detecting radiation emitted by the reference dye. In some embodiments, a method may further comprise; irradiating the mixture with a third excitation wavelength range, and detecting radiation emitted by at least a second reporter dye.

In some embodiments, a method may comprise: irradiating the mixture with a first excitation wavelength range; detecting radiation emitted by at least a first reporter dye; and detecting radiation emitted by at least a second reporter dye; wherein the radiation emitted by at least a first reporter dye can be detected separately from the radiation emitted by at least a second reporter dye.

According to various embodiments, a method can further comprise irradiating the nucleic acid-containing sample with a first excitation wavelength range, detecting radiation emitted from at least one dye of a plurality of dyes upon irradiation of the sample with the first excitation wavelength range, irradiating the sample with a second excitation wavelength range that differs from the first excitation wavelength range, and detecting radiation emitted from at feast one other of a plurality of dyes upon irradiation of the sample with the second excitation wavelength range. A different wavelength range for excitation can be used for each different reporter dye of the plurality of dyes, and for the passive reference dye.

In some embodiments a composition may be provided, wherein a composition comprises a master mix utilizing a reference dye of formula (I);

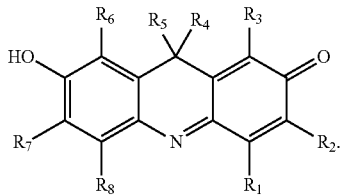

wherein:
each of $R_1$ to $R_3$ and $R_6$ to $R_8$ is independently —H, halogen, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_3$-$C_6$ alkyl, $C_1$-$C_6$ alkoxy, and substituted $C_1$-$C_6$ alkoxy, wherein R is $C_1$-$C_6$ alkyl, substituted $C_1$-$C_6$ alkyl, $C_1$-$C_6$ alkoxy, and substituted $C_1$-$C_6$ alkoxy;
$R_4$ and $R_5$ taken separately are selected from $C_1$-$C_6$ alkyl and $C_1$-$C_6$ substituted alkyl, and $R_4$ and $R_5$ taken together are selected from $C_3$-$C_7$ cycloalkyl, $C_4$-$C_7$ unsaturated cycloalkyl, $C_3$-$C_7$ substituted cycloalkyl or $C_4$-$C_7$ substituted unsaturated cycloalkyl.

In some embodiments, $R_1$ is selected from hydrogen, halogen, methyl, and ethyl; $R_2$ and $R_3$ are each independently a halogen; $R_4$ and $R_5$ are each independently selected from methyl and ethyl; $R_6$ is selected from hydrogen, halogen, methyl, and ethyl; $R_7$ is selected from hydrogen, halogen, methyl, ethyl, and $SO_3H$; and $R_8$ is selected from hydrogen, halogen, methyl, and ethyl. In some embodiments, $R_2$ and $R_3$ are each chlorine and $R_7$ is $SO_3H$. In some embodiments, the reference dye is selected from:

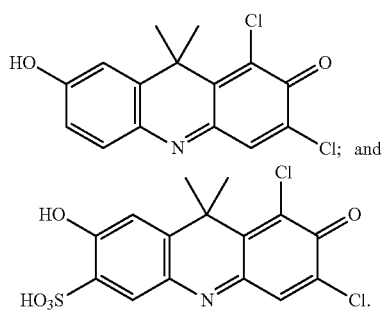

According to various embodiments, a master mix may contain a buffer, a selection at nucleotides, for example, but not limited by deoxynucleotides (dNTPS i.e. dATP, dGTP, dCTP, and TTP), primers, and at least one protein moiety. In various embodiments, a master mix may contain a buffer, a selection of nucleotides, for example, but not limited by, dNTPS (i.e. dATP, dGTP, dCTP, and TTP), primers, at least one protein moiety, and a reference dye. In various embodiments, a master mix may contain a buffer, a selection of nucleotides, for example, but not limited by, dNTPS (i.e. dATP, dGTP, dCTP, and TTP), and at least one protein moiety. In venous embodiments, a master mix may contain a buffer, a selection of nucleotides, for example, but not limited by, dNTPS (i.e. dATP, dGTP, dCTP, and TTP), at least one protein moiety, and a reference dye, in various embodiments, a master mix may be supped lyophilized or suspended in a buffer solution.

In some embodiments, a kit may include a reference dye of formula (1). In some embodiments, the reference dye may be an ingredient in a master mix in a kit. In some embodiments, the reference dye and a master mix maybe separate containers in a kit. In some embodiments the reference dye and each of the at least one probes may be in separate containers in a kit. In some embodiments, the reference dye may be in a master mix, and the master mix and each of the at least one probes are in separate containers in a kit. In some embodiments, the reference dye, a master mix, and each of the at least one probes may be in separate containers in a kit. In some embodiments, the reference dye and at least one of the probes may be in the same container in the kit. In some embodiments, at least two of the probes may be in the same container, while the reference dye is in a separate container in the kit. In various embodiments, the kit components may be supplied lyophilized or suspended in a buffer solution.

BRIEF DESCRIPTION OF THE DRAWINGS

FIG. 8 is a matrix of different mixtures of four reporter dye-labeled oligonucleotides and Sulfo-DDAO reference dye, which were mixed together in various concentrations to simulate different possible endpoint readings for genotyping assay signals, and to test the ability of Sulfo-DDAO to be used as a reference dye under each of the sixteen different simulated conditions.

FIGS. 9A and 9B show scatter plots of fluorescence signal intensities generated using pure dye mixtures from FIG. 8. FIG. 9A is a plot of reporter dyes FAM® and VIC® emissions, which were deconvolved from the background of reporter dyes TED® and SID® using Sulfo-DDAO as a reference dye. FIG. 9B is a plot of reporter dyes TED® and SID® emissions, which are deconvolved from the background of reporter dyes FAM® and VIC® using Suite-DDAO as a reference dye FIG. 10A is a plot of reporter dyes FAM® and VIC® emissions, which were deconvolved from the background of reporter dyes TED® and SID® using Sulfo-DDAO as a reference dye. FIG. 10B shows the inability to deconvolve reporter dyes FAM® and VIC® emissions in a background of reporter dyes TED® and SID®, using a ROX reference dye.

DETAILED DESCRIPTION

Figure 1:
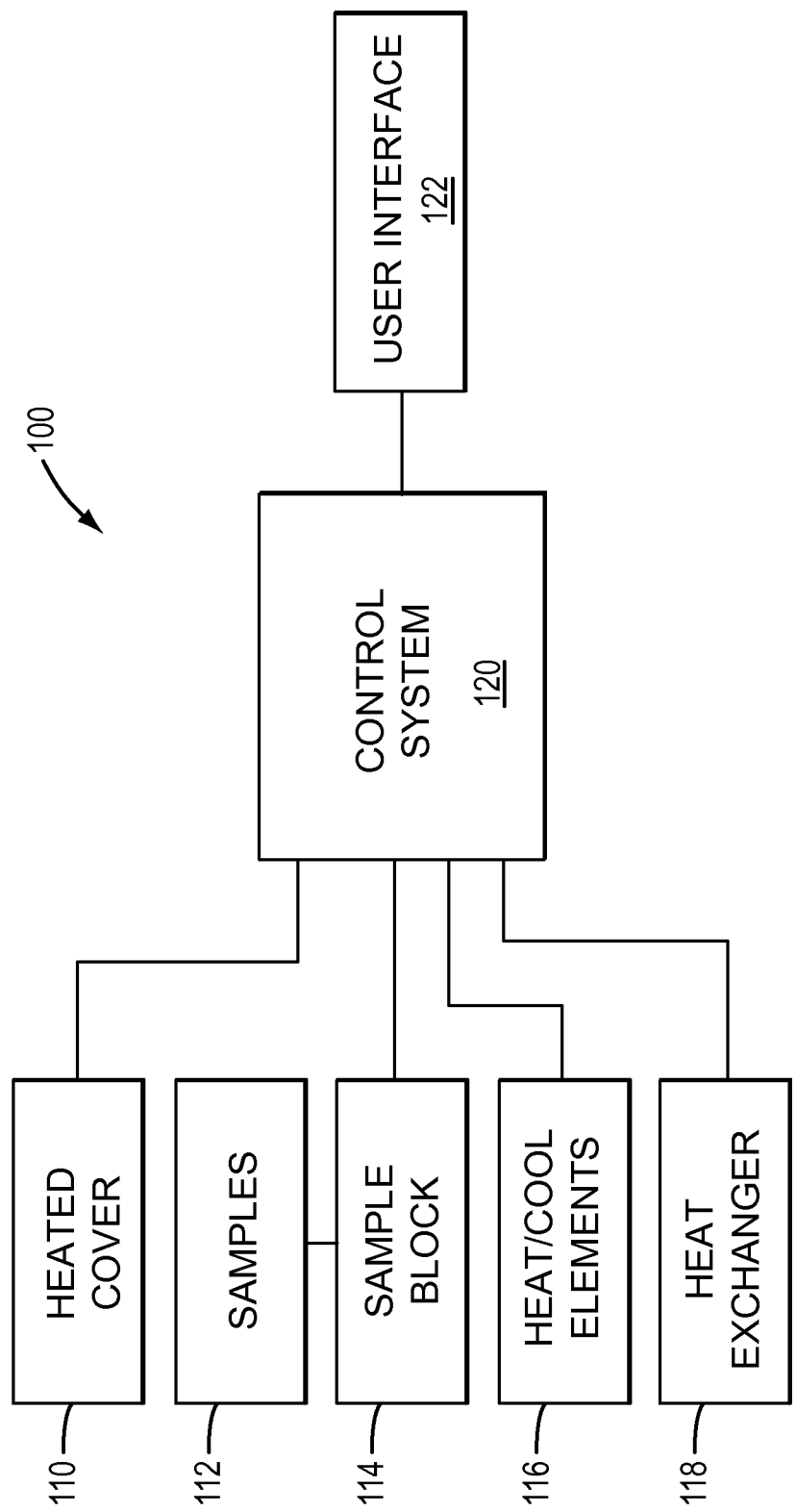
FIG. 1 is a block diagram of a PCR instrument according to various embodiments of methods of the present teachings.

According to various embodiments of methods and compositions of the present teachings, a reference dye is provided, wherein the reference dye is of formula (I):

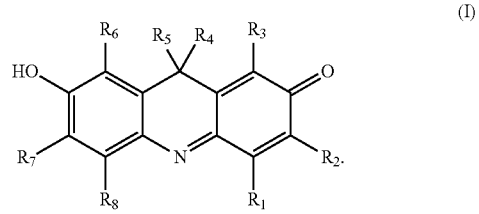

(I)

wherein:
each of R1 to R3 and R6 to R8 is independently —H, halogen, —CO2H, —CO2R, —SO3H, —SO3R, —CH2CO2H, —CH2CO2R, —CH2SO3H, —CH2SO3R, —CH2NH2, —CH2NHR, —NO2, C1-C6 alkyl, substituted C1-C6 alkyl, C1-C6 alkoxy, and substituted C1-C6 alkoxy, wherein R is C1-C6 alkyl, substituted C1-C6 alkyl, C1-C6 alkoxy, and substituted C1-C6 alkoxy.
R4 and R5 are either, taken separately, independently selected from a C1-C6 alkyl and a C1-C6 substituted alkyl, or, taken together, are C3-C7 cycloalkyl, C4-C7 unsaturated cycloalkyl, C3-C7 substituted cycloalkyl, or C4-C7 substituted unsaturated cycloalkyl.

As used herein, "substituted" refers to a molecule wherein one or more hydrogen atoms are replaced with one of more non-hydrogen atoms, functional groups or moieties. For example, unsubstituted amine is —NH$_2$, while on-limiting exemplary substituted amines include, but are not limited to, —NHCH$_3$ and —N(CH$_2$CH$_3$)$_2$. Similarly, an exemplary unsubstituted alkyl is —CH$_2$CH$_3$, while on-limiting exemplary corresponding substituted alkyls include, but are not limited to, —CH$_2$CH$_2$COOH, —CH(NH$_3$)CH$_3$, and —CH=CHOOCH$_3$. Exemplary substituents include, but are not limited to, halogen, fluorine, chlorine, bromine, $C_1$-$C_6$ alkyl, $C_1$-$C_6$ cycloalkyl, $C_1$-$C_6$ branched alkyl, $C_1$-$C_6$ alkene, $C_1$-$C_6$ cyclic alkene, $C_1$-$C_6$ branched alkene, $C_1$-$C_6$ alkyne, $C_1$-$C_6$ branched alkyne, carboxyl, ester, sulfate, sulfonate, sulfone, amino, ammonium, amido, nitrite. $C_1$-$C_6$ alkoxy, phenoxy, substituted phenoxy aromatic, phenyl, polycyclic aromatic, and electron-rich heterocycle.

In some embodiments, $R_1$ is hydrogen, halogen, methyl, or ethyl. In some embodiments, $R_2$ and $R_3$ are each independently a halogen. In some embodiments, $R_4$ and $R_5$ are each independently a methyl or ethyl. In some embodiments, $R_6$ is hydrogen, halogen, methyl, or ethyl. In some embodiments, $R_7$ is hydrogen, halogen, methyl, ethyl, or SO$_3$H. In some embodiments, $R_8$ is hydrogen, halogen, methyl, or ethyl. In some embodiments, $R_8$ is hydrogen, halogen, methyl, or ethyl; $R_2$ and $R_3$ are each independently a halogen; $R_4$ and $R_5$ are each independently a methyl or ethyl; $R_6$ hydrogen, halogen, methyl, or ethyl; $R_7$ is hydrogen, halogen, methyl, ethyl, or SO$_3$H and $R_4$ is hydrogen, halogen, methyl, or ethyl. In some such embodiments, $R_2$ and $R_3$ are each chlorine and $R_7$ is SO$_3$H.

In some embodiments, a reference dye is a congener of 7-hydroxy-9H-1,3-dichloro-9,9-dimethylacridin-2-one (DDAO). Exemplary reference dyes include, but are not limited to:

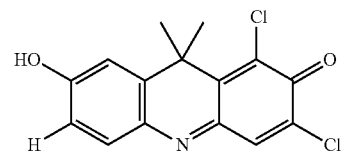 [SMILES: CC1(C)C2=C(Cl)C(=O)C(Cl)=CC2=Nc2ccc(O)cc21]

1,3-dichloro-7-hydroxy-9,9-dimethylacridin-2(9H)-one (DDAO), and

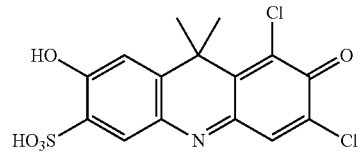 [SMILES: CC1(C)C2=C(Cl)C(=O)C(Cl)=CC2=Nc2cc(S(=O)(=O)O)c(O)cc21]

6,8-dichloro-2-hydroxy-9,9-dimethyl-7-oxo-7,9-dihydroacridine-3-sulfonic acid (Sulfo-DDAO).

Some attributes of reference dyes of formula (I) that are useful for a fluorescence reference dye in various methods and compositions of the present teachings may include, but are not limited by, high chemical and photochemical stability, fluorescent emission that is relatively constant over a wide temperature range, high water solubility, a broad adsorption spectrum, and a sharp emission spectrum that is spectrally distinguishable from the reporter dyes used in the assay. Further, an attribute of reference dye of formula (I) may include not interfering in an assay being performed, such as any of a variety of assays utilizing the polymerase chain reaction (PCR), and variations thereof. Dyes that may interfere in an assay may do so, by, for example, either interfering directly by inhibiting a reaction, or may interfere by, for example, by interacting with a probe dye.

The reference dyes of the present teachings may be used in any method in which a reference dye is desirable. Exemplary methods in which the reference dyes may be used include but are not limited to, methods involving polynucleotide detection, methods involving polynucleotide amplification, and methods involving target detection using oligonucleotides, antibodies, antigens, small molecules, polysaccharides, and the like. Non-limiting exemplary targets include but are not limited to, polynucleotides, antigens, antibodies, receptors, organelles, membranes, metabolites, enzymes, cells (such as eukaryotic and prokaryotic cells) and the like. Non-limiting exemplary polynucleotides include DNA and RNA from a variety of nucleic acid-containing samples.

A used herein, the term "nucleic acid-containing sample" refers to nucleic acid found in biological samples according to the present teachings. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used its broadest sense and refers to a sample containing a nucleic acid from which a gene target or target polynucleotide may be derived. A sample can comprise a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, plants, livestock, household pets, and human samples, and can be derived from a plurality of sources. These sources may include, but are not limited to, whole blood, hair, blood, urine, tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples, purified samples, and lysed cells. It will be appreciated that nucleic acid samples containing target polynucleotide sequences can be isolated from samples from using any of a variety of sample preparation procedures known in the art, for example, including the use of such procedures as mechanical force, sonication, restriction endonuclease cleavage, or any method known in the art.

The terms "target polynucleotide," "gene target", "target genomic locus" and the like as used herein are used interchangeably herein and refer to a particular nucleic acid sequence of interest. Such a target can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target" used in the context of a particular nucleic acid sequence of interest additionally refers to surrogates thereof, for example amplification products, and native sequences. In some embodiments, a particular nucleic acid sequence of interest is a short DNA molecule derived from a degraded source, such as can be found in, for example, but not limited to, forensics samples. A particular nucleic acid sequence of interest of the present teachings can be derived from any of a number of organisms and sources, as recited above. Regarding the ploidy state of a target genomic locus, for an organism with a diploid genome, in which two alleles define a locus, that there to three possible genotypes for such a diploid state. One of ordinary skill in the art will appreciate that any ploidy state is discretely associated with a finite number of allelic combinations defining a genotype classification. Thus, for any ploidy state for any sample having a target genomic locus of interest, there are a finite and calculable number of genotypes.

As used herein, "DNA" refers to deoxyribonucleic acid in its venous forms as understood in the art, such as genomic, DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

In some embodiments of methods and composition of the present teachings, the peak emission wavelength of a reference dye does not overlap with the peak emission wavelengths of the reporter dyes. The present methods may use reference dyes of formula (I), for example, in multiplex reactions. In various embodiments of methods and compositions, when multiplexing using spectrally distinct dyes, a reference dye is independently detectable from the reporter dyes used in the assay.

A multiplex assay may indicate the presence, absence, amount, and identity of at least two targets in a mixture and comprises at least two probes that indicate the presence, absence, amount, and identity of the same target in a mixture. In some embodiments, a multiplex assay is used to indicate the presence, absence, amount, and identity of, at least three, at least four, at least five, or at least six targets in a mixture. In various embodiments of methods and composition according to the present teachings, a multiplex assay may be performed in a sample array format. In such a multiplex method, multiple targets may be detected in a single sample region of a sample containment device. Such a multiplex method would be differentiated from far example, various sequencing methods, in which multiplex PCR is performed as a sample preparation step before sequencing is performed and detected. In various embodiments of methods and compositions of the present teachings, in which multiplex assay is performed in a sample array format, a reference dye of formula (1) may provide for up six or more reporter dyes to be used in such a multiplex assay.

In some embodiments, each of the different targets in the mixture is detected using a different reporter dye. In some embodiments, the same reporter dye maybe used on two or more different probes to detect the presence of a single target. In some embodiments, each reporter dye and the reference dye are detected separately, e.g., by irradiating the mixture at each excitation wavelength and detecting the radiation emitted by each reporter dye and the reference dye separately. In some embodiments, two or more of the reporter dyes and the reference dye are detected simultaneously, either by irradiating with more than one excitation wavelength simultaneously and detecting the radiation emitted by more than one of the reporter dyes and the reference dye simultaneously, or by irradiating with a single excitation wavelength that is absorbed by more than one of the reporter dyes and the reference dye, and then detecting radiation emitted by more than one of the reporter dyes and the reference dye simultaneously. In some embodiments, one or more of the reporter dyes are fluorescence resonance energy transfer (FRET) dyes. In some such embodiments, for example, when two of the reporter dyes are FRET dyes, both dyes may absorb at the same wavelength, but emit at different wavelengths. As will be discussed in more detail subsequently, selections of spectrally distinct sets of reporter and reference dyes according to formula (I) may be selected for use in various embodiments of methods and compositions according to the present teachings.

The term "reference dye" as used herein refers to a fluorescent dye of formula (I). In some embodiments, a reference dye is included in a mixture and is used to normalize the signals of other dyes (such as reporter dyes) in the assay and mixture. As one of ordinary skit in the art will appreciate, there are many variables in analysis that may impact variation of results. A reference dye detection signal may provide a reference signal that can be used to adjust the reporter dye detection signal to correct far fluctuation caused by experimental variation, such as pippeting, which may cause variations in sample concentration or volume, as well as system variation, such as of detection non-uniformity for reporter, reference and background signals, and of thermal non-uniformity. In various embodiments, adjusting a measured detection signal of a reporter dye may include dividing or subtracting a measured detection signal of a reference dye from a measured detection signal of a reporter dye, in various embodiments, adjusting a measured detection signal of a reporter dye may include any mathematical operation in which a measured detection signal of a reference dye is used to adjust a measured detection signal of a reporter dye.

In some embodiments, a reference dye is included in each mixture of a set of mixtures and may be used to normalize across mixtures. For example, in some embodiments, a reference dye may be included in all of the wells of a multiwell plate (such as a 96-well plate) and may be used to normalize the effect of well position on fluorescent signal detection. In various embodiments of methods and compositions according to the present teachings a reference dye of formula (I) may be used as a "free dye," meaning that it is not conjugated to another molecule, such as another dye or an oligonucleotide.

The term "reporter dye" as used herein refers to a moiety that is used in a mixture to indicate the presence, absence, amount, activity, and identity of a target in the mixture. Reporter dyes may include, but are not limited to, fluorescent dyes and particles, phosphorescent dyes and particles, quantum dots, lanthanides, and chemi-luminophores. A reporter dye may be a fluorescence resonance energy transfer (FRET) dye or a non-FRET dye. In some embodiments, a reporter dye may be linked to a moiety selected from an oligonucleotide, a peptide, an antibody, a small molecule, and a polysaccharide, wherein the moiety imparts specificity on the reporter dye. In some embodiments, the reporter dye linked to the moiety that imparts specificity is referred to as a "probe." In some embodiments, the reporter dye indicates the presence, absence, amount, activity, and identity of a target molecule in the assay, wherein the moiety that imparts specificity on the reporter dye is specific for the target molecule.

The term "probe," as used herein, refers to a molecule comprising a target-specific moiety and at least one reporter dye, which is used to detect the presence, absence, amount activity, and identity of a target in a mixture. The target-specific moiety may be linked to at least one reporter dye either covalently or noncovalently. Non-limiting exemplary target-specific moieties include oligonucleotides peptides, antibodies, antigens, small molecules, and polysaccharides. In various embodiments, a probe comprising a peptide and a reporter dye may be referred to as a "labeled peptide;" a probe comprising an antibody and a reporter dye may be referred to as a "labeled antibody," a probe comprising an antigen and a reporter dye may be referred to as a "labeled antigen;" a probe comprising a small molecule and a reporter dye may be referred to as a "labeled small molecule;" and a probe comprising a polysaccharide end a reporter eye may be referred to as a "labeled polysaccharide."

As used herein, the terms "amplifying", "amplification," and related terms refer to any process that increases the amount of a desired nucleic acid. Any of a variety of known amplification procedures may be employed in the present teachings, including, but not limited to, PCR (see, for example, U.S. Pat. No. 4,663,202), including quantitative and real-fine PCR, as well as any of a variety of ligation-mediated approaches, including LDR and LCR (see, for example, U.S. Pat. Nos. 5,494,810; 5,830,711; and 6,054,564). Additional non-limiting amplification procedures include, but are net limited to, isothermal approaches such as rolling circle amplification and helicase-dependant amplification. One of skill in art will readily appreciate a variety of possible amplification procedures applicable in the context of the present teachings.

In some embodiments, a probe comprises an oligonucleotide and at least one reporter dye may be used in an amplification reaction. In some embodiments, a probe comprises an oligonucleotide, a reporter dye, and a quencher dye. In some such embodiments, such as a TaqMan® probe, degradation a the oligonucleotide portion of the probe separates the reporter dye from the quencher dye and results in a detectable signal from the reporter dye. In some embodiments, a probe comprises two hybridized oligonucleotides one of which comprises a reporter dye and the other of which comprises a quencher dye such that when the oligonucleotides are hybridized, the reporter dye signal is quenched. In some embodiments, such as in the presence of a target that hybridizes to one of the probe oligonucleotides, the reporter dye and the quencher dye are separated such that a signal is detectable from the reporter dye.

Non-limiting exemplary probes include, but are not limited to, TaqMan® probes (see, e.g., U.S. Pat. No. 5,538,648), stem-loop molecular beacons (see, e.g., U.S. Pat. Nos. 6,103, 476 and 5,925,517 and Tyagi and Kramer, 1996, *Nature Biotechnology* 14:303-308), stemless or linear beacons (see, e.g., WO 99/21881). PNA molecular beacons (see, e.g., U.S. Pat. Nos. 6,355,421 and 6,593,091), linear PNA beacons (see, e.g., Kubista at al., 2001, SPIE 4264:53-58), non-FRET probes (see, e.g., U.S. Pat. No. 6,150,097), Sunrise®/Amplifluor® probes (see, e.g., U.S. Pat. No. 6,548,250), stem-loop on duplex Scorpion™ probes (see, e.g., Sclinas et al. 2001, *Nucleic Acids Research* 29:E96 and U.S. Pat. No. 6,589,743), bulge loop probes (see, e.g., U.S. Pat. No. 6,590,091) pseudo knot probes (see, e.g., U.S. Pat. No. 6,589,250), cyclicons (see, e.g., U.S. Pat. No. 6,383,752). MGB Eclipse™ probes (Epoch Biosciences), hairpin probes (see, e.g., U.S. Pat. No. 6,596,490), peptide nucleic acid (PNA) light-up probes, self-assembled nanoparticle probes, and ferrocene-modified probes. See, e.g., U.S. Pat. No. 6,485,901; Mhlanga et al., 2001. *Methods* 25:463-471; Whitcombe et al., 1999, *Nature*

Biotechnology. 17:804-807; Isacsson et al., 2000, *Molecular Cell Probes*. 14:321-328, Svanvik et al., 2000, *Anal Biochem*. 281:26-35: Wolffs et al., 2001, *Biotechniques* 766:769-771, Tsourkas et al., 2002, *Nucleic Acids Research*. 30:4208-4215; Riccelli et al., 2002, *Nucleic Acids Research* 30:4088-4093; Zhang at al., 2002 *Shanghai*. 24:329-332; Maxwell et al., 2002, *J. Am. Chem. Soc.* 124:9606-9612; Broude et al., 2002, *Trends Biotechnol.* 20:249.56; Huang et al., 2002, *Chem Res. Toxicol.* 15:118-126; and Yu et al., 2001, *J. Am. Chem. Soc* 14:11155-11161. In some embodiments, probes comprise black hole quenchers (Biosearch), Iowa Black (IDT), QSY quencher (Molecular Probes), and Dabsyl and Dabcel sulfonate/carboxylate Quenchers and Epoch quenchers. Labeling probes can also comprise two probes, wherein for example a fluorophore is on one probe, and a quencher on the other, wherein hybridization of the two probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a labeling probe.

In some embodiments, a probe comprising an oligonucleotide and a reporter dye may be referred to as a "labeled oligonucleotide." Further, the oligonucleotide portion of the labeled oligonucleotide may be of any length, such as at least 5, a least 6, at least 7, at least 8, at least 9, at least 10, at least 12, at least 15, at least 20, at least 25, at least 30, at least 35, at least 40, at least 50, at least 59 at least 70, at least 80, at least 90, at least 100, at least 120, at least 150, at least 200, etc., nucleotides in length. The oligonucleotide portion of the labeled oligonucleotide may comprise deoxyribonucleic acid (DNA), ribonucleic acid (RNA), peptide nucleic acid (PNA), derivatives of any of the foregoing, and combinations of any of the foregoing. Regardless of the composition of the oligonucleotide, each unit of the oligonucleotide that is equivalent to a DNA or RNA base is referred to as a "nucleotide."

According to various embodiments of methods and compositions of the present teachings, a spectrally distinguishable set of reporter dyes and a reference dye according to formula (1) may be used in various assays, such as, but not limited by, various amplification assays, in which a thermal cycling instrument may be utilized.

According to various embodiments of a thermal cycler instrument 100, as shown in FIG. 1, a thermal cycling instrument may include a heated cover 110 that is placed over a plurality at samples 112 contained in a sample support device. Same examples of a sample support device may include, but are not limited to, tubes, vials, and a multi-welt plate permitting a selection of sample capacities, such as a standard microtiter 96-well, a 384-well plate. In various embodiments, a sample support device may be a micro device capable of processing thousands of samples per analysis, such as various microfluidic devices, microcard devices, and micro chip devices. In various embodiments, a sample support device may be a fabricated from a substantially planar support, such as a glass, metal or plastic slide, having a plurality of sample regions. The sample regions in various embodiments of a sample support device may include through-holes, depressions, indentations, and ridges, and combinations thereof, patterned in regular or irregular arrays formed on the surface of the substrate. In various embodiments, a sample support device may have a cover between the sample regions and heated cover 110. A sample support device may have sample regions arranged in a sample array format. One of ordinary skill in the art will recognize that many examples of a sample support device are patterned in row and column arrays. A sample array format according to the present teachings may include any pattern of convenient and addressable arrangement of sample regions in a sample support device, including a single row or column of sample regions in a sample support device.

In venous embodiments of a thermal cycler instrument 100, include a sample block 114, an element or elements for heating and cooling 116, and a heat exchanger 118. Various embodiments of a thermal block assembly according to the present teachings comprise components 114-118 of thermal cycler system 100 of FIG. 1.

Figure 2:
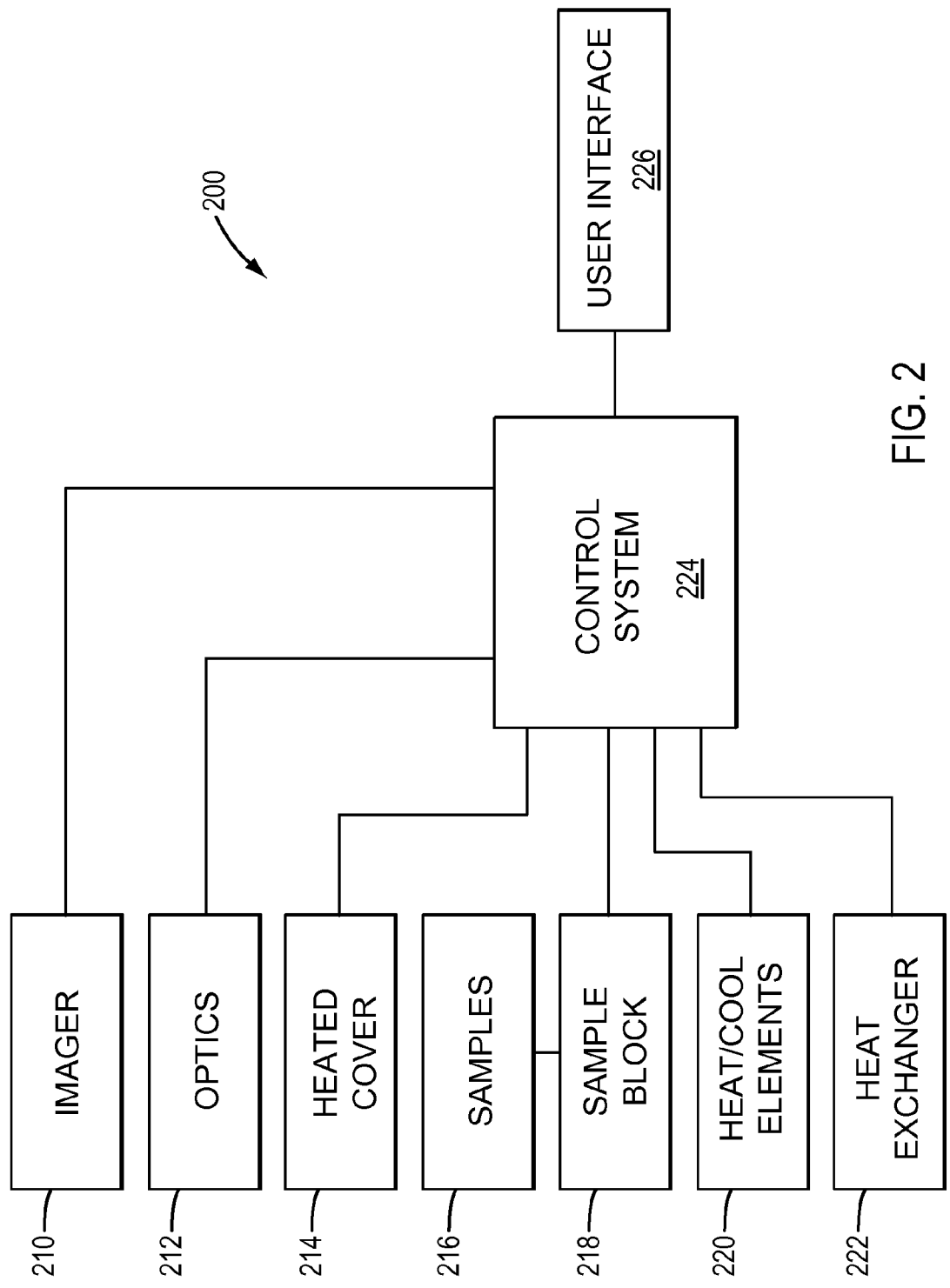
FIG. 2 is a block diagram of a PCR instrument according to various embodiments of methods of the present teachings.

In FIG. 2, various embodiments of a thermal cycling system 200 have the components of embodiments of thermal cycling instrument 100, and additionally a detection system comprising, an imager 210 and optics 212. It should be noted that while a thermal cycler system 200 is configured to detect signals from samples in a sample support device during an analysis, a detection system according to the present teachings may be used detect signals from a thermal cycler system 100 after an analysis has been completed.

A detection system may have an electromagnetic radiation source that emits electromagnetic energy, and a detector or imager 210, for receiving electromagnetic energy from samples 216 in sample support device. A detector or imager 210 may capable of detecting electromagnetic energy from samples 216 may a charged coupled device (CCD), back-side thin-cooled COD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and manipulation of data for example, a computer, or other signal processing system. Additionally, optics 212 of a detection system may include components, such as, but not limited by, various positive end negative lenses, mirrors, and excitation and emission filters.

Regarding various embodiments of an electromagnetic radiation source for a detection system, such sources may include but are not limited to, white light, halogen lamps, lasers, solid state lasers, laser diodes, micro-wire lasers, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, floodlight systems using LEDs, and white LEDs, filament lamps, arc lamps, gas lamps, and fluorescent tubes. Light sources can have high radiance, such as lasers, or low radiance, such as LEDs. The different types of LEDs mentioned above can have a medium to high radiance.

Multiple excitation and emission filter sets can be employed in existing thermal cycling devices, wherein each filter set may include pre-selected excitation and emission filters to provide an accurate response of signal proportional to oligonucleotide concentration in a sample at various stages of PCR. The excitation filter in a coupled set of filters can be chosen to allow wavelengths of light received from the light source that are close to the peak excitation wavelength of a predetermined dye to pass. The excitation filter can also be configured to block wavelengths of light that are greater than and less than the peak excitation wavelength. Similarly, the emission filter in the set of filters can be chosen to allow light close to the peak emission wavelength to pass while also blocking wavelengths outside the peak emission wavelength. In such a fashion, and as will be discussed in more detail subsequently, a selection of spectrally distinguishable dye species, in conjunction with the detection system, and data processing capabilities of a thermal cycling apparatus may provide for detection of a plurality of dye signals in, for example, a multiplex assay.

In use, detection system for use with a thermal cycling device may function by impinging an excitation beam from an electromagnetic radiation source on samples in a sample support device, thereby generating a fluorescent radiation from the plurality of samples 116, 216. Light emitted from the samples 112, 216, may be transmitted trough a lens or lenses, such as a well lens, a Fresnel lens, or a field lens, and then may be directed to additional optical components, such as a dichroic mirror, and an emission filter. Undesired wavelengths of light emitted from the samples 112, 216, may be reflected by the dichroic mirror or are blocked by the emission filter. A portion of the emitted light that transmits through the dichroic mirror and emission filter may be received by a detector or imager 210. For a thermal cycler system 100, a detector or imager may generate data signals from the fluorescent radiation from the samples at the completion of a PCR assay. For a thermal cycler system 200, a detector or it 210 may generate data signals from the fluorescent radiation from the samples over time from which the concentration of target DNA in the samples at the particular stage of PCR may be determined.

Figure 3:
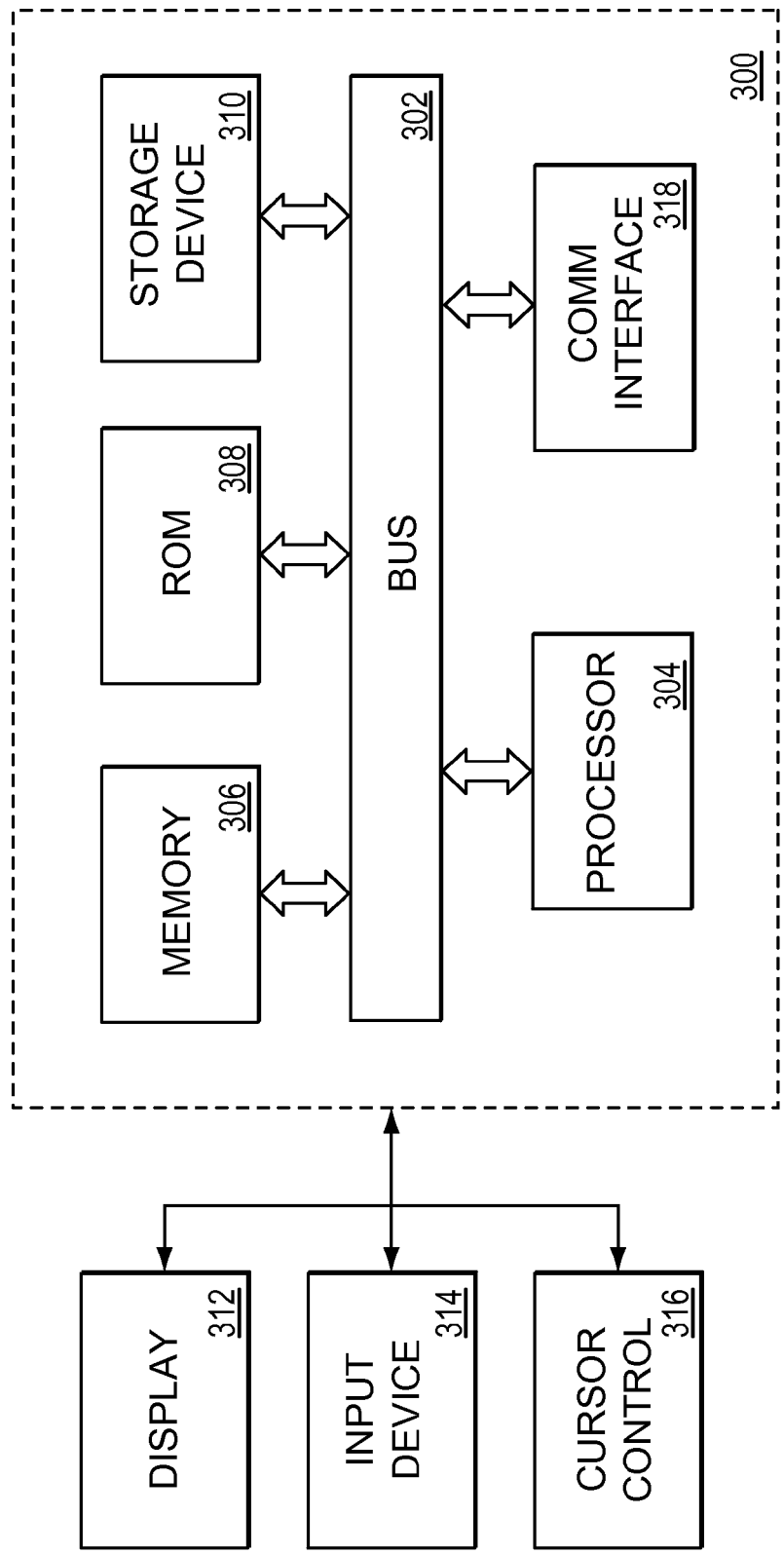
FIG. 3 is a block diagram that illustrates components of an exemplary computer system that may be utilized in the control and interlace of the PCR instrumentation according to various embodiments of methods of the present teachings.

For embodiments of thermal cycler instrumentation 100 and 200, a control system 120 and 224, respectively, may be used to control the functions of the detection, heated cover, and thermal block assembly. The control system may be accessible to an end user through user interface 122 of thermal cycler instrument 100 and 224 of thermal cycler instrument 200. A computer system 300, as depicted in FIG. 3 may serve as to provide the control the function of a thermal cycler instrument, as well as the user interface function. Additionally, computer system 300 may provide data processing, as well as, with other components, provide for display and report preparation functions. For example, signals received by a detector or imager may be processed by various algorithms, such as a spectral deconvolution algorithm, which may then be displayed to an end user, as well as providing a report. All such instrument control functions may be dedicated locally to the thermal cycler instrument, or computer system 300 may provide remote control of part or all or the control, analysis, and reporting functions as will be discussed in more detail subsequently.

FIG. 3 is a block diagram that illustrates a computer system 300, according to various embodiments, upon which embodiments of a thermal cycler system 100 of FIG. 1 or a thermal cycler system 200 of FIG. 2 may utilize. Computer system 300 includes a bus 302 or other communication mechanism for communicating information, and a processor 304 coupled with bus 302 for processing information. Computer system 300 also includes a memory 306, which can be a random access memory (RAM) or other dynamic storage device, coupled to bus 302 for instructions to be executed by processor 304. Memory 306 also may be used for storing temporary variables or other intermediate information during execution of instructions to be executed by processor 304. Computer system 300 further includes a read only memory (ROM) 308 or other static storage device coupled to bus 302 for storing static information and instructions for processor 304. A storage device 310 such as a magnetic or optical disk, is provided and coupled to bus 302 for storing information and instructions.

Computer system 300 may be coupled via bus 302 to a display 312, such as a cathode ray tuba (CRT) or liquid crystal display (LCD), for displaying information to a computer user. An input device 314, including alphanumeric and other keys, is coupled to bus 302 for communicating information and command selections to processor 304. Another type of user input device is cursor control 316, such as a mouse, a trackball or cursor direction keys for communicating direction information and command selections to processor 304 and for controlling cursor movement on display 312. This input device typically has two degrees of freedom in two axes, a first axis (e.g., x) and a second axis (e.g., y), that allows the device to specify positions in a plane. A computer system 300 provides data processing and provides a level of confidence for such data. Consistent with certain implementations of the present teachings, data processing and confidence values are provided by computer system 300 in response to processor 304 executing one or more sequences of one or more instructions contained in memory 306. Such instructions may be read into memory 306 from another computer-readable medium, such as storage device 310. Execution of the sequences of instructions contained in memory 306 causes processor 304 to perform the process states described herein. Alternatively hardwired circuitry may be used in place of or in combination with software instructions to implement various embodiments of methods and compositions of the present teachings. Thus implementations of the present teachings are not limited to any specific combination of hardware circuitry and software.

The term "computer-readable medium" as used herein refers to any media that participates in providing instructions to processor 304 for execution. Such a medium may take many forms, including but not limited to, non-volatile media, volatile media, and transmission media. Non-volatile media includes, for example, optical or magnetic disks, such as storage device 310. Volatile media includes dynamic memory, such as memory 306. Transmission media includes coaxial cables, cooper wire, and fiber optics, including the wires that comprise bus 302. Transmission media can also take the form of acoustic or light waves, such as those generated during radio-wave and infra-red data communications. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Further, it should be appreciated that a computer 300 of FIG. 3 may be embodied in any of a number of forms, such as a rack-mounted computer, a desktop computer, a laptop computer, or a tablet computer. According to various embodiments of a computer 300 of FIG. 3, a computer may be embedded in any number or mobile and web-based devices not generally regarded as a computer but with suitable processing capabilities. Example of such devices may include, but are not limited by a Personal Digital Assistant (PDA), a smart phone, and a notepad any other suitable electronic device. Additionally, a computer system can include a conventional network system including a client/server environment and one or more database servers. A number of conventional network systems, including a local area network (LAN) or a wide area network (WAN), and including wireless and wired components, are known in the art. Additionally, client/server environments, database servers, and networks are well documented in the art.

As previously discussed, a reference dye selected from members of the family of dyes represented by formula (I) below have a number of desirable attributes that make them useful candidates as a reference dye:

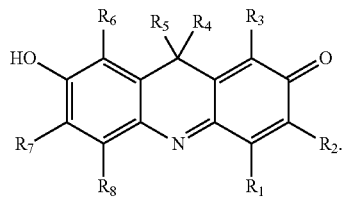
(I)

wherein:
each of $R_1$ to and $R_3$ and $R_6$ to $R_8$ is independently —H, halogen, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, and substituted $C_1$-$C_6$ alkoxy, wherein R is $C_1$-$C_6$ alkyl, substituted $C_1$-$C_6$ alkyl, $C_1$-$C_6$ alkoxy, and substituted $C_1$-$C_6$ alkoxy;

$R_4$ and $R_5$ are either, taken separately, independently selected from a $C_1$-$C_6$ alkyl and a $C_1$-$C_6$ substituted alkyl, or, taken together, are $C_3$-$C_7$ cycloalkyl, $C_4$-$C_7$ unsaturated cycloalkyl, $C_3$-$C_7$ substituted cycloalkyl, $C_4$-$C_7$ substituted unsaturated cycloalkyl.

In some embodiments, a reference dye is a congener of 7-hydroxy-9H-1,3-dichloro-9,9-dimethylacridin-2-one (DDAO). Exemplary reference dyes include, but are not limited to:

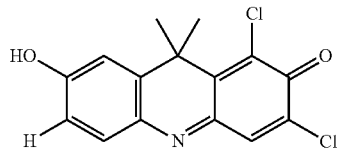

1,3-dichloro-7-hydroxy-9,9-dimethylacridin-2(9H)-one (DDAO), and

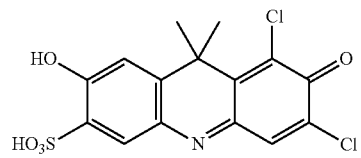 [SMILES: CC1(C)C2=C(Cl)C(=O)C(Cl)=CC2=Nc2cc(S(=O)(=O)O)c(O)cc21]

6,8-dichloro-2-hydroxy-9,9-dimethyl-7-oxo-7,9-dihydroacridine-3-sulfonic acid (Sulfo-DDAO).

Figure 4:
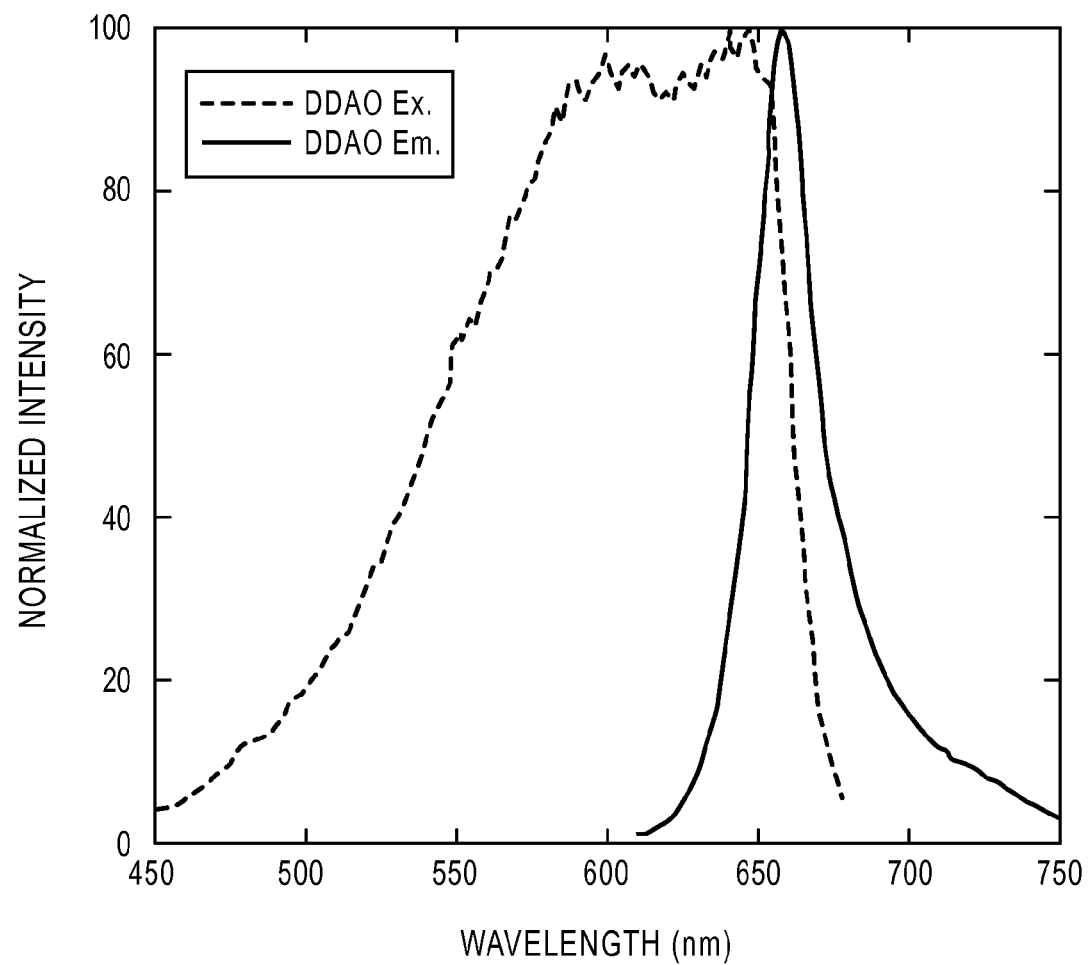
FIG. 4 is a graph snowing the fluorescence emission and excitation spectra of DDAO, which may be used as a reference dye according to various embodiments of the present teachings.
Figure 5:
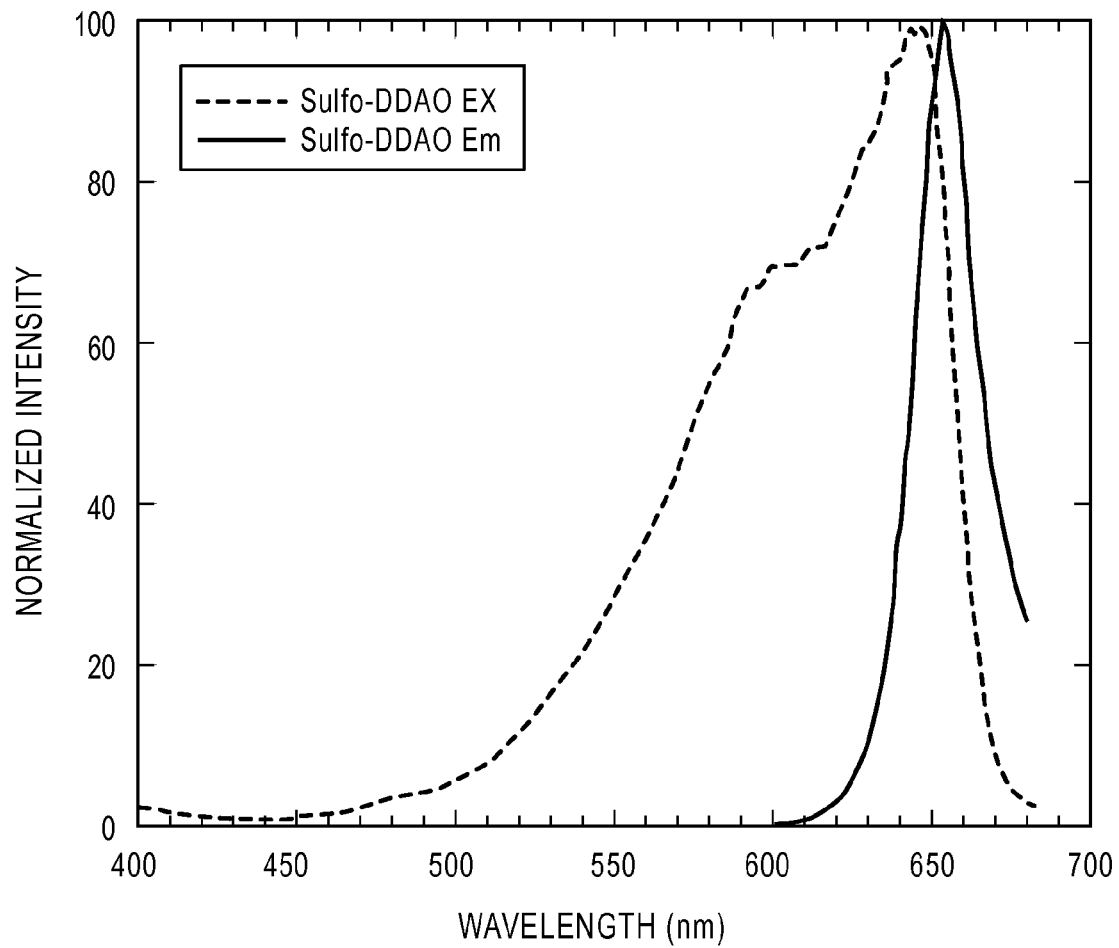
FIG. 5 is a graph showing the fluorescence emission and excitation spectra of Sulfo-DDAO, which may be used as a reference dye according to various embodiments of the present teachings.

For example, FIG. 4 and FIG. 5 show the normalized emission and excitation spectra of DDAO and Sulfo-DDAO, respectively. The spectra were normalized by setting the maximum for each spectrum at 100 units prior to plotting. While DDAO and Sulfo-DDAO are exemplified in FIG. 4 and FIG. 5, respectively, it is to be understood that any of the reference dyes of formula (I) can be used in the present methods, including, for example, other congeners of DDAO.

As shown in FIG. 4 and FIG. 5, the excitation and emission spectra of DDAO and Sulfo-DDAO show that the reference dyes absorb very long wavelengths, with peak absorption at about 640 nm. In that regard, DDAO and Sulfo-DDAO also emit at very long wavelengths, with peak emission at about 650 to 660 nm, that regard, DDAO, and congeners thereof, such Sulfo-DDAO violate the mirror image rule, and have a unique signature in the excitation and emission spectra. Because the excitation spectrum is broad and the emission spectrum is compact DDAO and its congeners, such as, for example, the compounds of formula (I) are suitable for use with a broad range of excitation source wavelengths as reference dyes the presence of reporter dyes, for example, that absorb and emit at shorter wavelengths. Moreover, congeners of DDAO have an emission hand that allows a wider selection of reporter dyes of interest to be spectrally resolved when dyes of formula (1) are used as a reference dye.

Further, as will be discussed in more detail subsequently, compounds of formula (I) have high water solubility, readily allowing for a range of concentrations in aqueous-based solutions and reagents. Additionally, compounds of formula (I) have high chemical and photochemical stability, stable fluorescence emission over a broad range of temperatures, and do not interfere with various biochemical assays, such as PCR. Accordingly, compounds of formula (I) are particularly well suited as reference dyes in bioanalysis.

Figure 6:
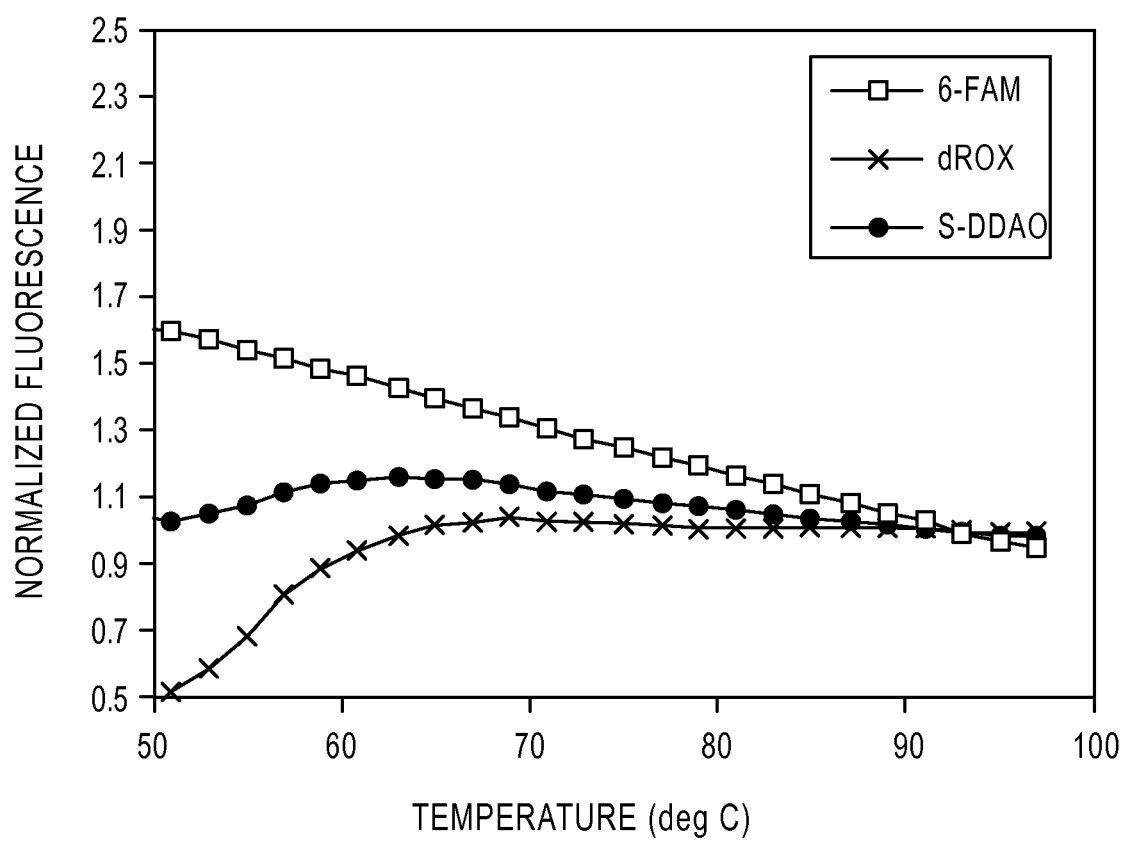
FIG. 6 a graph thawing the fluorescent emission signal detected as a function of temperature for Sulfo-DDAO in comparison: to two other dyes.

FIG. 6 depicts a graph of normalized fluorescent emission as a traction of temperature for Sulfo-DDAO in comparison to a reporter dye, 6-FAM, as well as a reference dye, ROX. Given the difference in brightness of the dyes shown, each data point for each curve was adjusted using an internal reference point taken from the 94° C. data point for that data set. In that regard, the fluorescence signals are normalized to give equal intensities at 94 C so that their relative changes with temperature can be easily compared. As can be seen from the data, the fluorescence emission is fairly stable across a wide range of temperatures for Sulfo-DDAO. This attribute may be useful when, for example, dye calibration they be one at a different temperature from a run temperature, or could be useful for normalizing experimental variations as previously discussed.

Figure 7:
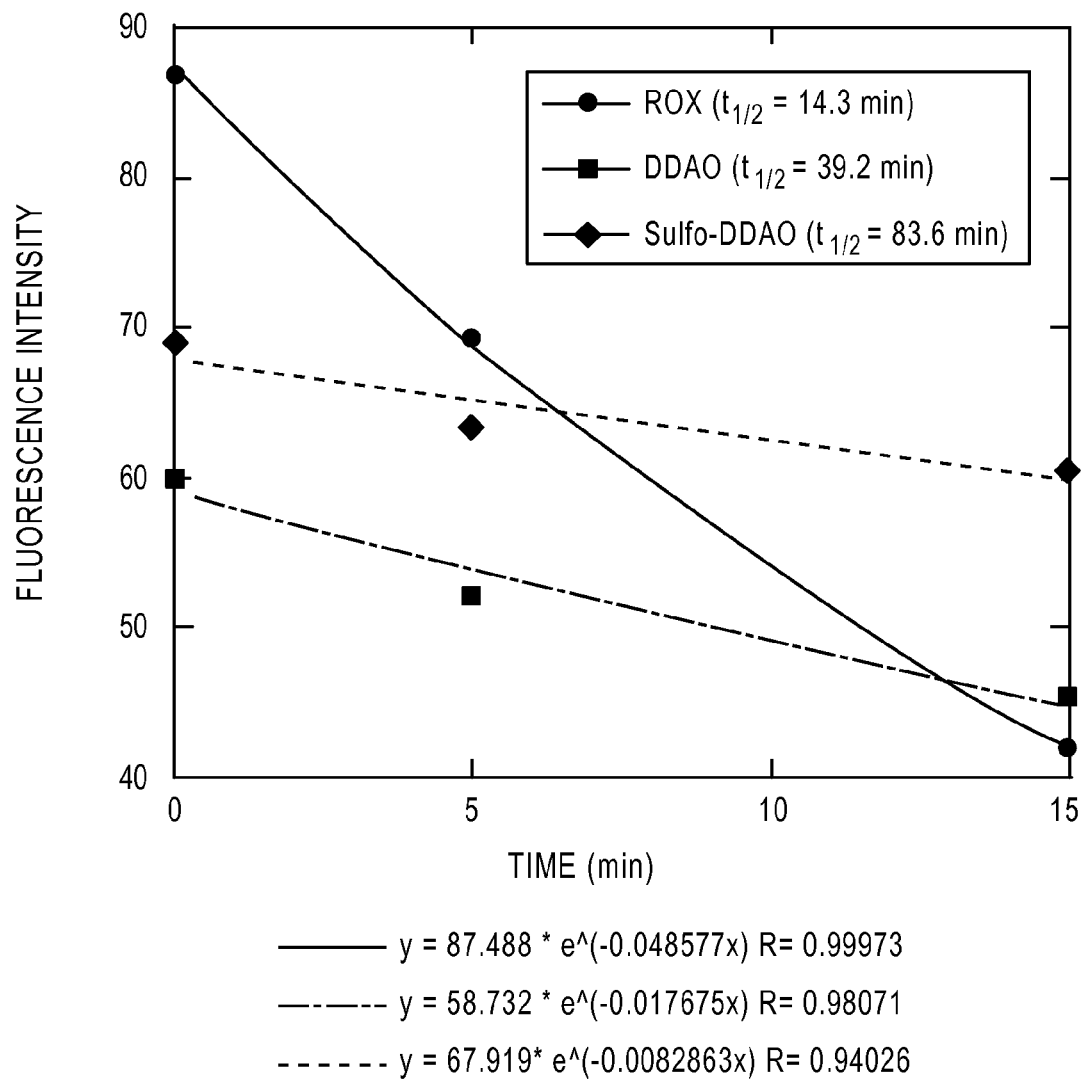
FIG. 7 is a graph showing the chemical stability of reference dyes according to the present teachings.

Regarding chemical stability, DDAO congeners appear to have resilience under various conditions, such as oxidation, photo-degradation, and the like. For example, regarding resilience to harsh oxidation, DDAO, Sulfo-DDAO, and ROX were each suspended as free dyes in a solution of 1.4 of Tris-EDTA buffer (1× stock concentration) in MeOH at a concentration of approximately 1 µM. Five µl of 0.5M benzoyl peroxide in acetonitrile was added to 1 ml of the dye composition in a fluorimeter cuvette. Fluorescence emission intensity was measured at each dye's emission maximum immediately, and then at 5 minute intervals. A first-order exponential curve was fit to the data to calculate the decay rate for each dye. FIG. 7 is a graph showing the results of that experiment. As shown in that figure, both DDAO and Sulfo-DDAO show resilience to oxidation in comparison to ROX. As such, the reference dyes of formula (I) can be used in assays in which the assay components might come in contact with oxidants.

The matrix shown in FIG. 8 was used to test whether Sulfo-DDAO can be used in a genotyping assay as a reference dye without interfering with spectral separator of all possible genotyping signals for a multiplex; in this example, a duplex assay. Four reporter dyes, namely, FAM, VIC, TED, and SID, were used in various mixtures with Sulfo-DDAO as a reference dye. Although no sample was used in the assays, the concentrations of the reporter dyes were controlled to simulate 16 different combinations of genotyping signals, as would be collected, processed and displayed by a thermal cycling apparatus. For the mixtures where a particular reporter dye was used as a background, the reporter dye was used at a low level as an unquenched dye, to simulate an uncleaved probe signal when combined with the Sulfo-DDAO reference dye. For mixtures where the reporter dye was used to generate a SIGNAL, the concentration was 10-fold higher compared to the concentration when used as a background, to simulate a cleaved probe signal. The SIGNAL concentration was meant to mimic a positive test for a specific genotype.

Figures 10A, 10B:
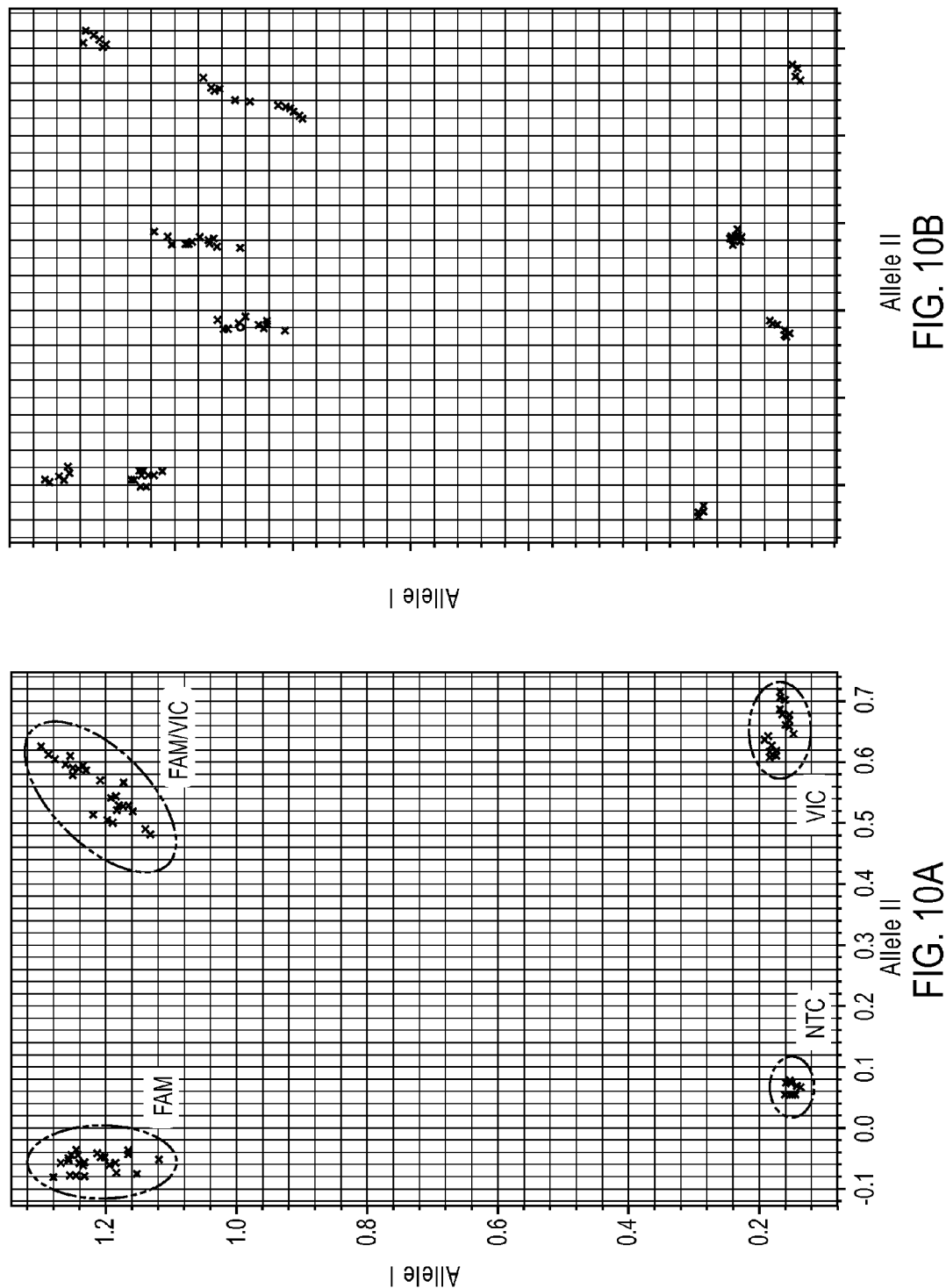
FIGS. 10A and 10B show scatter pilots of fluorescence signal intensities generated using pure dye mixtures from FIG. 8.

Data generated from the deconvoluted signals resulting from the various mixtures shown in FIG. 8 is shown as scatter plots in FIGS. 9A and 9B. The data show good spectral separation for all mixtures, with well-resolved signals for each positive signal represented by clusters in the upper left and lower right and negative background signals representing non-template control (NTC) in the lower left cluster. In each reaction well the simulated genotype could be correctly called for both the FAM/VIC genotyping pair and for the TED/SID genotyping pair when they are used together in the same assay with Sulfo-DDAO as the passive reference. Similarly, the experiments outlined in the matrix of FIG. 8 were done using another reference dye, ROX. FIG. 10B shows signal detected for a FAM/VIC genotyping pair in the presence of TED/SID background signal (similar to FIG. 10A), but with a ROX passive reference. Poor spectral separation was observed, resulting in false positive signets. FIGS. 9A and 9B, in comparison to FIG. 10B demonstrate the impact of selection of an appropriate reference dye; particularly in a multiplex assay, where the reaction matrix is more complex than in an assay where a single probe is used. It should be specifically noted that the red-shifted position of the Sulfo-DDAO emission enabled the selection of four spectrally separated reporter dyes; providing for a set of five spectrally distinct dyes.

Additionally, a variety of physico-chemical forces, such as, but not limited by, Lifschitz-van der Waals, London dispersion, hydrogen, and ionic forces, may act to promote dye-dye interactions, such as ring stacking. Such dye-dye interactions may produce untoward results for a variety of assays, such as a variety of assays based on PCR and related reactions. The data generated in the model study additionally suggests that DDAO congeners do not promote untoward interactions with various reporter dyes.

As one of ordinary skill in the art is apprised, a master mix is a composition that may contain almost all of the ingredients required for an amplification reaction except for the sample. The use of a master nix affords both efficiency and consistency in performing a plurality of amplification reactions on a plurality of sample regions of a sample support device. In venous embodiments a master mix may contain a buffer, a selection of nucleotides, for example, but not limited by, deoxynucleotides (dNTPS i.e. dATP, dGTP, dCTP, and TTP), primers, and at least one protein moiety. In various embodiments, a master mix may contain a buffer, a selection of nucleotides, for example but not limited by, dNTPS (i.e. dATP, dGTP, dCTP, and TTP), primers, at least one protein moiety, and a reference dye. In various embodiments, a master mix may contain a buffer, a selection of nucleotides, for example, but not limited by, dNTPS (i.e. dATP, dGTP, dCTP, and TTP), and at least one protein moiety. In various embodiments, a master mix may contain a buffer, a selection of nucleotides, for example, but not limited by, dNTPS (i.e. dATP, dGTP, dCTP, and TTP), at least one protein moiety, and a reference dye. In various embodiments, a master mix may be supplied lyophilized or suspended in a buffer solution.

According to various embodiments of a master mix, a buffer may be selected, for example, but not limited by tris, as well as a variety of Good's buffers, such as, tricene, bicene, HEPES, and MOPS. In various embodiments, the buffer may also contain essential non-buffering ingredients, such as various salts, surfactants, and as well as other. Examples of essential non-buffering ingredients may include, but are not limited by, chloride salts of sodium, potassium, lithium, magnesium and manganese, as well as surfactants, such as but not limited by, polysorbate surfactants (e.g. Tween 20 and Tween 80), polyoxyethylene surfactants (e.g. Brij 56 and Brij 58), polyethoxylated phenol surfactants (e.g. NP-40 and Triton X100), and zwitterionic surfactants (e.g. CHAPS, CHAPSO, Big-CHAP). Additional buffer ingredients may include, for example, but not limited by glycerol, ethylene glycol, propylene glycol, and various molecular weights of polyethylene glycol. According to various embodiments of a master mix, nucleotides may be selected, for example, but not limited by, from dNTPs (i.e. dATP, dGTP, dCTP, and TTP), dideoxynucleotides (didNTPs), deaze-GTP, deaza-dGTP, and 2'-deoxyinosine 5'-triphosphate (dITP). For various embodiments of a master mix, a protein moiety may be selected, for example, but not limited by, from a DNA polymerase, a ligase, a reverse transcriptase, a ribonuclease (e.g. RNase H), a glycosylase (e.g. uracil-N-glycosylase), a single strand binding protein (e.g. GP32), a pyrophosphatase (e.g. from *Thermoplasma acidophilum*), an albumin, and a gelatin.

Figure 11:
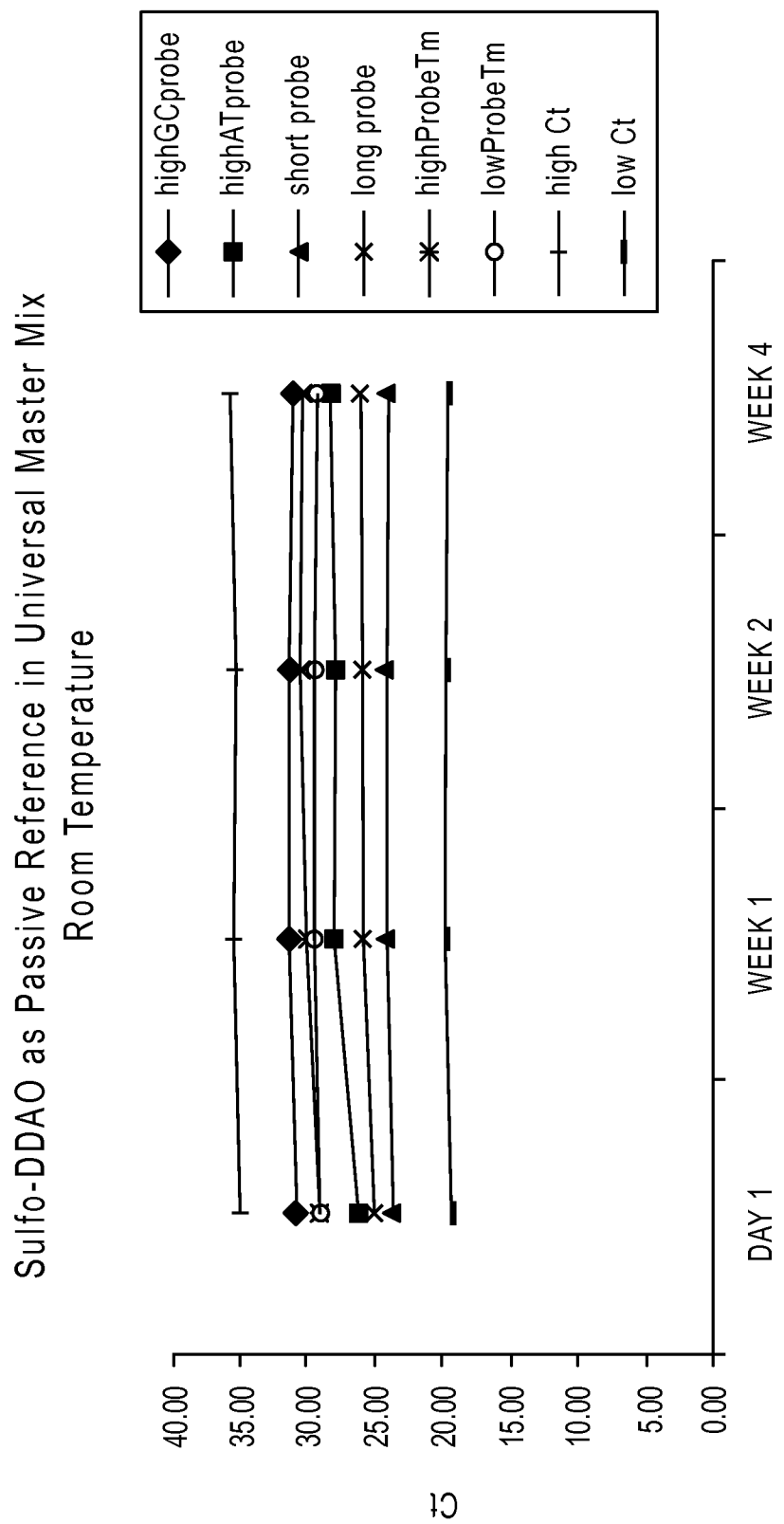
FIG. 11 is a graph showing the chemical stability of Sulfo-DDAO, when used as a reference dye in a universal master mix, measured over a four-week period as measured by assay activity, and in the presence of a variety of different types of probes.

FIG. 11 depicts the stability of Sulfo-DDAO in a master mix, and incubated with various additional additives. Sulfo-DDAO was incubated in TaqMan® Universal PCR Master Mix at room temperature for 1 day, 1 week, 2 weeks, or 4 weeks. At each designated time point, fixed quantities of various, different target polynucleotides and various dye-labeled TaqMan® probes, were added. The target/probe mixtures were PCR amplified in a 96 well plate and the signals recorded after each amplification cycle to generate an amplification count from which a Ct value was determined for each target/probe mixture, using Sulfo-DDAO as a reference dye. FIG. 11 is a graph showing the results of that experiment, with the Ct values plotted for each time point. The Sulfo-DDAO signal was stable at room temperature in TaqMan® Universal PCR Master Mix for up to 4 weeks, as evidenced by the consistent Ct values obtained at different incubation times for the different target/probe mixtures, using Sulfa-DDAO as a reference dye. Further, Sulfo-DDAO did not interfere with the amplification of the various target polynucleotides.

Non-limiting exemplary reporter dyes that can be used, in various embodiments, in the present methods and kits include any of those described, for example, in Menchen, et al., U.S. Pat. No. 5,188,934; Benson, at al., U.S. Pat. No. 6,020,481; Lee, et al., U.S. Pat. No. 5,847,162; Benson, et al., U.S. Pat. No. 6,008,379; Benson, et al., U.S. Pat. No. 5,936,087; Upadhya, et al., U.S. Pat. No. 6,221,604; Lee, et al., U.S. Pat. No. 6,191,278; Yan, et al., U.S. Pat. No. 6,140,500; Mao et al., U.S. Pat. No. 6,130,101; Glazer, et al., U.S. Pat. No. 5,853, 992; Brush, et al., U.S. Pat. No. 5,986,086; Hamilton, et al., U.S. Pat. No. 6,140,494; Hermann, et al., U.S. Pat. No. 5,750, 409; Haugland et. al., U.S. Pat. No. 5,248,782; and Karolin et al., *JACS* 116: 7801-6 (1994), each of which is incorporated by reference in its entirety with regard to fluorescent dye structures, fluorescent dye synthesis, fluorescent dye conjugation to biopolymers, application of fluorescent dyes in energy transfer dyes, and fluorescent dye spectral properties.

Exemplary reporter dyes also include, but are not limited to, fluorescein dyes such as 5- and 6-carboxyfluorescein (5- and 6-FAM), 5- and 6-carboxy-2',4',5',7',-4,7-hexachlorofluorescein (5- and 6-HEX®), 5- and 6-carboxy-2',4',5',7'-tetrachlorofluorescein (5- and 6-TET®), NED®, PET®, 1,2'-benzo-4'-fluoro-7',4,7-trichloro-6-carboxy-fluoroscein, 1',2',7',8'-dibenzo-4,7-dichloro-5-carboxyfluorescein. Exemplary reporter dyes also include, but are not limited to, rhodamine dyes such as rhodamine green (rhodamine R110), 5-carboxyrhodamine, 6-carboxyrhodamine, N,N'-diethyl-2',7'-dimethyl-5-carboxy-rhodamine (5-R6G), N,N'-diethyl-2',7'-dimethyl-6-carboxyrhodamine (6-R6G), N,N,N',N'-tetramethyl-5-carboxyrhodamine (5-TAMRA), N,N,N',N'-tetramethyl-6-carboxyrhodamine (6-TAMRA), 5-carboxy-X-rhodamine (5-ROX), and 6-carboxy-X-rhodamine (6-ROX). Exemplary reporter dyes include, but are not limited to, Alexa dyes such as Alexa Fluor® 488, Alexa Fluor® 514, Alexa Fluor® 555, Alexa Fluor® 568, Alexa Fluor® 594, and Alexa Fluor® 610. Exemplary reporter dyes include, but are not limited to, BODIPY dyes such as BODIPY Fl, BODIPY R6G, and BODIPY TMR. Exemplary reporter dyes also include, but are not limited to, quantum dots. FluoroSpheres, and fluorescent microspheres.

Certain on-limiting exemplary reporter dyes are shown in Table 1.

TABLE 1

| Reporter Dye | Absorbance (nm) | Emission (nm) | Extinction Coefficient |
|---|---|---|---|
| Pyrene | 341 | 377 | 43000 |
| 7-methoxycoumarin-3-carboxylic acid | 358 | 410 | 26000 |
| ALEXA FLUOR ® 405 | 401 | 421 | 35000 |
| Cascade Blue | 399 | 423 | 30000 |
| AMCA-X (Coumarin) | 353 | 442 | 19000 |
| ALEXA FLUOR ® 350 | 346 | 442 | 19000 |
| Pacific Blue | 416 | 451 | 37000 |
| Marina Blue | 362 | 459 | 19000 |
| 7-diethylaminocoumarin-3-carboxylic acid | 432 | 472 | 56000 |
| EDANS | 336 | 490 | 5700 |
| Syto 9 | 483 | 503 | 65,000 |
| BODIPY 493/503 | 500 | 509 | 79000 |
| BODIPY FL-X | 504 | 510 | 70000 |
| BODIPY FL | 504 | 510 | 70000 |
| Oregon Green 488 | 496 | 516 | 76000 |
| 6-Carboxyfluorescein (6-FAM) | 494 | 518 | 80000 |
| Oregon Green 500 | 499 | 519 | 84000 |
| ALEXA FLUOR ® 488 | 495 | 519 | 71000 |
| 5-Fluorescein | 495 | 520 | 73000 |
| Sybr Green | 494 | 521 | 73,000 |
| 5-Carboxyfluorescein (5-FAM) | 494 | 522 | 83000 |
| PicoGreen | 502 | 523 | Not available |
| Oregon Green 514 | 506 | 526 | 85000 |
| Rhodamine Green-X | 503 | 528 | 74000 |
| R110 | 501 | 529 | 75300 |
| DY-505 | 505 | 530 | 85000 |
| Lucifer Yellow | 428 | 532 | 11000 |
| NBD-X | 466 | 535 | 22000 |
| BigR110 | 504 | 537 | 115000 |
| dR110 | 520 | 538 | 70000 |
| 6-Carboxytetrachlorofluorescein (6-TET) | 521 | 538 | 87000 |
| ALEXA FLUOR ® 430 | 434 | 541 | 16000 |
| 5(6)-Caboxyeosin | 521 | 544 | 95000 |
| Erythrosin | 529 | 544 | 90000 |
| BODIPY R6G | 528 | 547 | 70000 |
| 5-R6G | 534 | 549 | 92300 |
| JOE ® | 528 | 550 | 80000 |
| VIC ® | 532 | 552 | 97000 |
| 6-Carboxyhexachlorofluorescein (6-HEX) | 535 | 553 | 71000 |
| ALEXA FLUOR ® 532 | 532 | 554 | 81000 |
| 5-Carboxyrhodamine 6G | 524 | 557 | 102000 |
| Cascade Yellow | 409 | 558 | 24000 |
| ALEXA FLUOR ® 555 | 555 | 565 | 150000 |
| Big R6G | 502 | 567 | 80000 |
|  | 548 |  | 89000 |
| dR6G | 548 | 567 | 91200 |
| BODIPY 564/570 | 563 | 569 | 142000 |
| BODIPY-TMR-X | 544 | 570 | 56000 |
| Cy3 | 552 | 570 | 150000 |
| PyMPO | 415 | 570 | 26000 |
| Oyster 556 | 556 | 570 | 155000 |
| NED ® | 546 | 573 | 69000 |
| Cy3B | 558 | 573 | 130000 |
| ALEXA FLUOR ® 546 | 556 | 573 | 104000 |
| 5-Carboxytetramethylrhodamine (5-TAMRA) | 546 | 576 | 90000 |
| 6-Carboxytetramethylrhodamine (6-TAMRA) | 544 | 576 | 90000 |
| DY-550 | 553 | 578 | 122000 |
| Rhodamine Red-X | 560 | 580 | 129000 |

TABLE 1-continued

| Reporter Dye | Absorbance (nm) | Emission (nm) | Extinction Coefficient |
|---|---|---|---|
| DY-555 | 555 | 580 | 100000 |
| 6-TAMRA | 560 | 582 | 97000 |
| TED ® | 496 | 583 | 89000 |
|  | 568 |  | 90900 |
| ABY ® | 568 | 583 | 90900 |
| BODIPY 581/591 | 581 | 591 | 136000 |
| Big TAMRA | 499 | 594 | 80000 |
|  | 577 |  | 90000 |
| dTAMRA | 578 | 594 | 97000 |
| PET ® | 558 | 595 | 88000 |
| Cy3.5 | 581 | 596 | 150000 |
| 5-Carboxy-X-Rhodamine (5-ROX) | 576 | 601 | 82000 |
| Dye 3.5 | 586 | 603 | 124000 |
| TAZ ® | 499 | 603 | 90000 |
|  | 586 |  | 124000 |
| Texas Red-X | 583 | 603 | 116000 |
| ALEXA FLUOR ® 568 | 578 | 603 | 91300 |
| 6-Carboxy-X-Rhodamine (6-ROX) | 587 | 607 | 117000 |
| BODIPY TR-X | 588 | 616 | 68000 |
| ALEXA FLUOR ® 594 | 590 | 617 | 73000 |
| dROX | 604 | 617 | 108000 |
| JUN ® | 606 | 618 | 128900 |
| SID ® | 499 | 618 | 91100 |
|  | 606 |  | 128900 |
| BigROX | 501 | 619 | 87000 |
|  | 605 |  | 115000 |
| DY-610 | 606 | 636 | 140000 |
| LIGHTCYCLER ™ Red 640 | 625 | 640 |  |
| BODIPY 630/650 | 625 | 640 | 101000 |
| ALEXA FLUOR ® 660 | 663 | 690 | 132000 |
| Cy5.5 | 675 | 694 | 250000 |
| DY-675 | 674 | 699 | 110000 |
| DY-676 | 674 | 699 | 84000 |
| ALEXA FLUOR ® 680 | 679 | 702 | 184000 |
| LIGHTCYCLER ™ Red 705 | 685 | 705 |  |
| WellRED D3-PA | 685 | 706 | 224000 |
| DY-681 | 691 | 708 | 125000 |
| DY-700 | 702 | 723 | 96000 |
| ALEXA FLUOR ® 700 | 702 | 723 | 192000 |
| DY-701 | 706 | 731 | 115000 |
| DY-730 | 734 | 750 | 113000 |
| WellRED D2-PA | 750 | 770 | 170000 |
| ALEXA FLUOR ® 750 | 749 | 775 | 240000 |
| DY-750 | 747 | 776 | 45700 |
| DY-751 | 751 | 779 | 220000 |
| DY-782 | 782 | 800 | 102000 |

As one skilled in the art will appreciate, a set of dyes can be configured to include a passive reference dye according to the present teachings and one or more of the many dyes listed in Table 1 as reporter dyes, to achieve a plurality of dyes that are each independently spectrally distinguishable from the other dyes of the set. One skilled in the art can select a suitable set of reporter dyes and at least one reference dye of formula (I), according to the intended application. One or more of the selected reporter dyes may be from the lists and patents discussed herein, or may be any other reporter dyes known in the art. In some embodiments, a spectrally distinguishable set of reporter dyes is chosen. In some embodiments, each dye in an assay has a peak emission wavelength that may be at least 5 nm, at least 10 nm, at least 15 nm, at least 20 nm, or least 30 nm from the peak emission wavelength of any of the other dyes in the assay. As previously discussed, the spectral separation of the dyes, in conjunction with various embodiments of a detection system and computational means allowing for data processing may together provide for various analyses, such s multiplexing.

Various embodiments of methods and compositions according to the present teachings comprise measuring fluorescence emitted by the reference dye. In some embodiments, the method comprises measuring fluorescence emitted by at least one reporter dye. In some such embodiments, the fluorescence may be emitted under excitation conditions suitable for the dye whose fluorescence is being measured. In some embodiments, the method further comprises normalizing the measured fluorescence emitted by at least one reporter dye based on the measured fluorescence emitted by the reference dye, to form a normalized measurement. The normalized measurement for each reporter dye can then be compared to the normalized measurement for one or more other reporter dyes in the reaction. Further, in some embodiments, one or more of the normalized measurements can be printed out, displayed, stored, or otherwise manipulated.

In some embodiments, a reaction mixture for an assay may comprise at least one, at least two, at least three, at least four, at least five, or at least six different reporter dyes that are each spectrally separated from one another, as well as a reference dye. In some embodiments, the reaction mixture may comprise at least one, at least two, at least three, at least four, at least five, or at least six different probes. In various embodiments, the mixture comprises one to six, one to five, one to four, two to six, two to five, two to four, three to six, three to five, or three to four distinct probes. In some embodiments, a probe is a labeled oligonucleotide. In some embodiments, a probe is a labeled peptide, a labeled antibody, a labeled antigen, a labeled small molecule, or a labeled polysaccharide.

In some embodiments, the method comprises irradiating the mixture with a first excitation wavelength and detecting light emitted horn at least a first reporter dye. In some embodiments, the method comprises irradiating the mixture with a second excitation wavelength, and detecting light emitted from at least a second reporter dye. In some embodiments, the second excitation wavelength differs from the first excitation wavelength. In some embodiments, a different excitation wavelength is used for each different reporter dye in the mixture, and for the reference dye. In some embodiments, the same excitation wavelength may be used for more than one reporter dye and reference dye in the mixture, although each of the more than one reporter dye and reference dye in the mixture can be distinguished by their emissions. That is, in some embodiments, multiple excitation wavelengths may be used simultaneously to excite more than one reporter dye and reference dye at the same time. Further, in some embodiments, following excitation, while the emission spectra of more than one reporter dye in the mixture may overlap, there is at least one wavelength for each dye at which that dye is the predominant emitter and therefore that dye is spectrally distinct and can be detected separately from the others at least that wavelength.

In some embodiments, one or more excitation wavelengths may be generated from an electromagnetic radiation source. In some embodiments, such an electromagnetic radiation source may be used to excite one or more reporter dyes and reference dyes. The method comprises, in some embodiments, actuating a broad wavelength emitting source and spectrally separating excitation beams from the light source to form at least two excitation sources of at least two different respective excitation wavelength ranges. In some embodiments, for simultaneous excitation of two or more dyes, the method can comprise forming at least two different, non-overlapping excitation wavelength ranges, at the same time.

In some embodiments, each dye can emit light, upon excitation, within a respective peak emission wavelength range, for example, having a width of about 10 nm centered at a peak emission wavelength of the dye, in some embodiments, each dye emits light within a respective peak emission wavelength range having a width in a range of about 5 nm-30 nm centered at a peak emission wavelength of the dye. The dyes can be selected, in some embodiments, such that the respective peak emission wavelength of each dye does not overlap with the peak emission wavelength of any of the other dyes in the mixture. The dyes can be selected in some embodiments, such that the respective emission decay rates of each dye is different from any of the other dyes in the mixture. To distinguish the emission of the reference dye from the emissions of the reporter dyes, in some embodiments, the fluorescence generated by the reference dye can be filtered using a first optical filter, and the fluorescence generated by at least one reporter dye can be filtered using a second optical fitter that differs in band pass from the first optical filter. In some embodiments, the first optical filter and the second optical fitter can together comprise a single filter.

Exemplary sets of spectrally distinguishable reporter dyes, with which a reference dye of formula (I) may be used, include, hut are not limited to, 6-FAM™, VIC®, TED®, TAZ®, and SID®, 6-FAM®, VIC®, ABY®, JUN®, and Dye 3.5; 6-FAM, TET®, HEX®, ABY®, Dye 3.5, and JUN®; and 6-FAM™, VIC®, NED®, and PET®. In some embodiments, each dye of the plurality of dyes can emit radiation, upon excitation, within a respective peak emission wavelength range. The dyes can be selected such that they are spectrally distinguished so that the respective peak emission wavelength range of each dye does not overlap with the peak emission wavelength range of any of the other dyes of the plurality. In some embodiments, one or more of the reporter dyes have a peak emission wavelength that is shorter than the peak emission wavelength of the reference dye. In some embodiments, one or more of the reporter dyes have a peek emission wavelength that is longer than the peak emission wavelength of the reference dye. For the purpose of illustration, non-limiting examples are given in FIG. 12-16.

Figure 12:
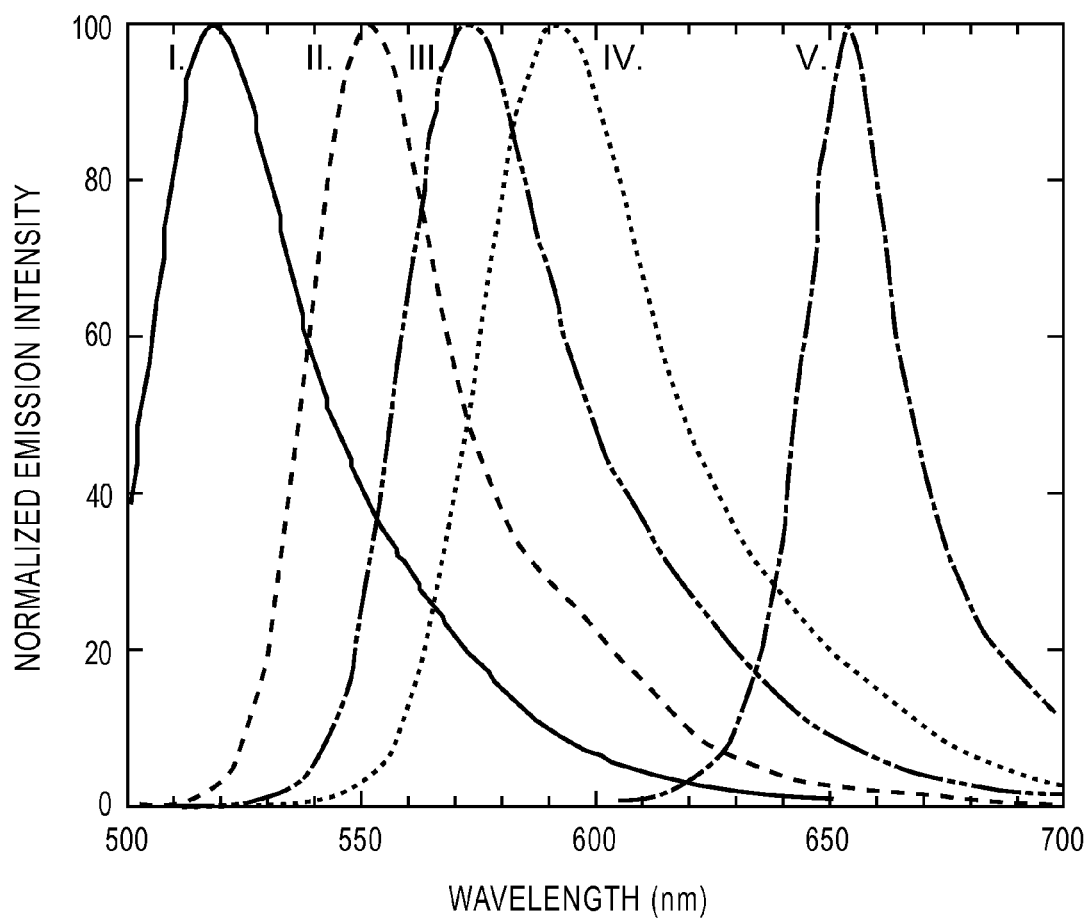
FIG. 12 shows the normalized fluorescence emission spectra of each dye of a set of dyes according to various embodiments of the present teachings, wherein the set includes Sulfo-DDAO as a reference dye and four reporter dyes of shorter emission wavelengths.

FIG. 12 shows an exemplary normalized emission spectrum of each dye in a on-limiting exemplary set of four reporter dyes with Sulfo-DDAO as a reference dye. The four reporter dyes are 6FAM™, VIC®, NED®, and PET®, which have peak emissions of 518, 552, 573, and 595 nm, respectively. Each dye is conjugated to an oligonucleotide, and the spectra are taken at 1 µM in Tris-EDTA buffer (1× stock concentration). The reference dye is Sulfo-DDAO and is not conjugated to an oligonucleotide. FIG. 12 shows an exemplary peak emission separation that can be achieved between a suitable set of reported dyes and the reference dye. Other sets reporter dyes can be chosen from the many possibilities described herein and known in the art.

Figure 13:
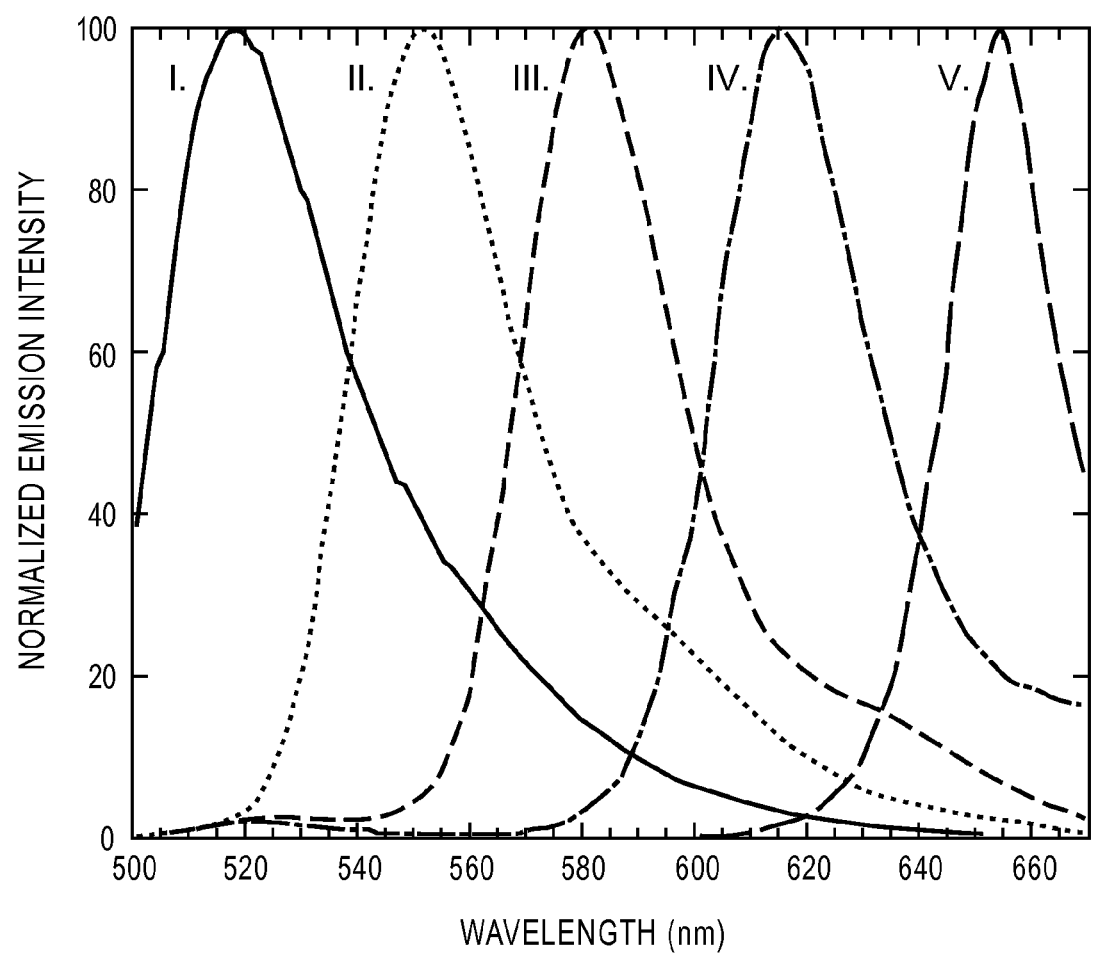
FIG. 13 shows a graph of normalized fluorescence emission spectra for a set of dyes according to various embodiments of the present teachings, wherein, the set comprises Sulfo-DDAO as a reference dye and four reporter dyes of shorter emission wavelengths.
Figure 14:
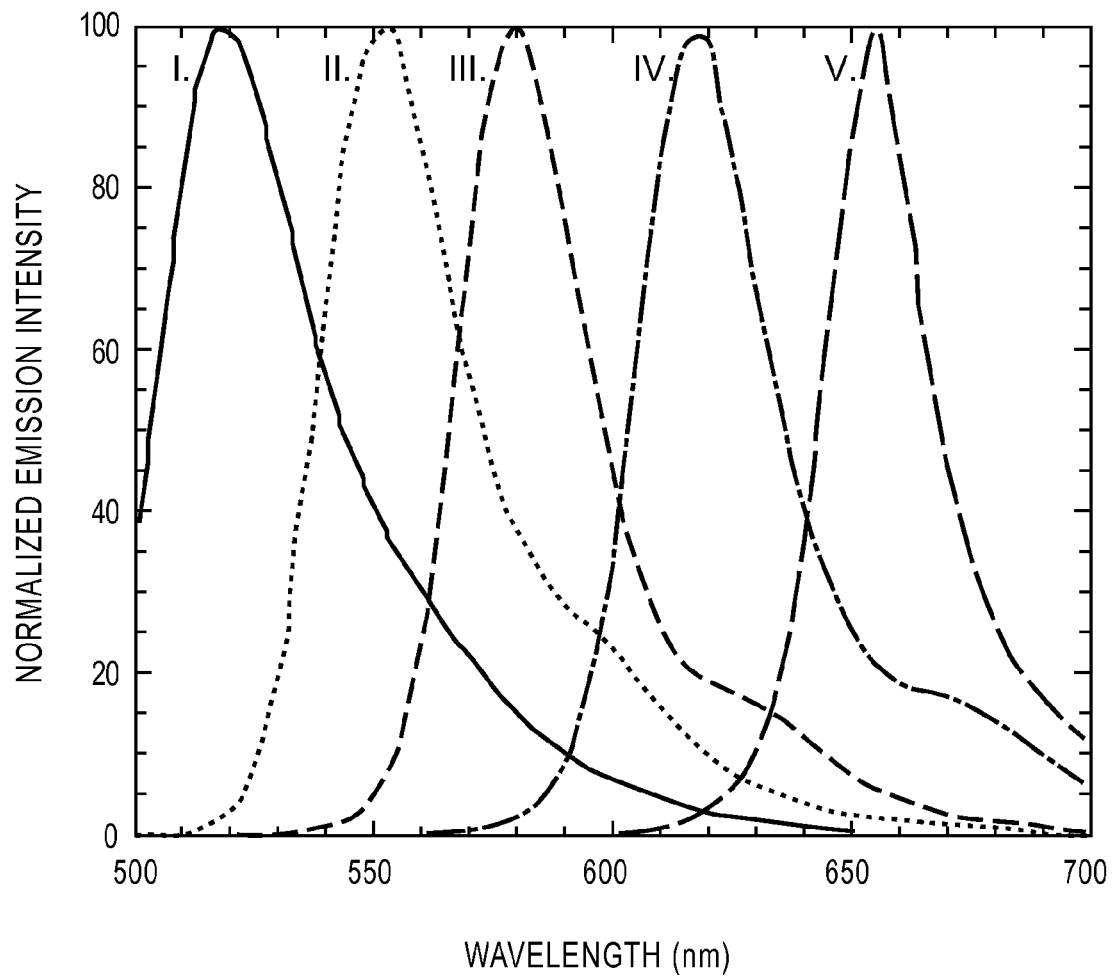
FIG. 14 shows a graph or normalized fluorescence emission spectra for a set of dyes according to various embodiments of the present teachings, wherein the set comprises Sulfo-DDAO as a reference dye and four reporter dyes of shorter emission wavelengths.

FIG. 13 shows the normalized emission intensify of each dye or a set of dyes according to venous embodiments of the present teachings, wherein the set includes Sulfo-DDAO as a passive reference dye and four reporter dyes of shorter emission wavelengths. The four reporter dyes are 6FAM™, VIC®, TED®, and SID®, which have peak emissions of 518, 552, 583, and 618 nm, respectively. Each dye is conjugated to an oligonucleotide, and the spectra are taken at 1 µM in Tris-EDTA buffer (1× stock concentration). The reference dye is Sulfo-DDAO, is a free dye and is not conjugated to an oligonucleotide. FIG. 13 shows an exemplary peak emission separation that can be achieved between a suitable set of reported dyes and the reference dye. Similarly, FIG. 14 shows a graph of normalized emission intensity for a set of dyes according to various embodiments of the present teachings, wherein the set comprises Sulfo-DDAO as a passive reference dye and four reporter dyes of shorter wavelengths. The four oligonucleotide-bound reporter dyes shown are 6-FAM™, VIC®, ABY®, and JUN®, which have peak emissions of 518, 552, 583, end 618 nm, respectively. Other sets reporter dyes can be chosen from the many possibilities described herein and known in the art.

Figure 15:
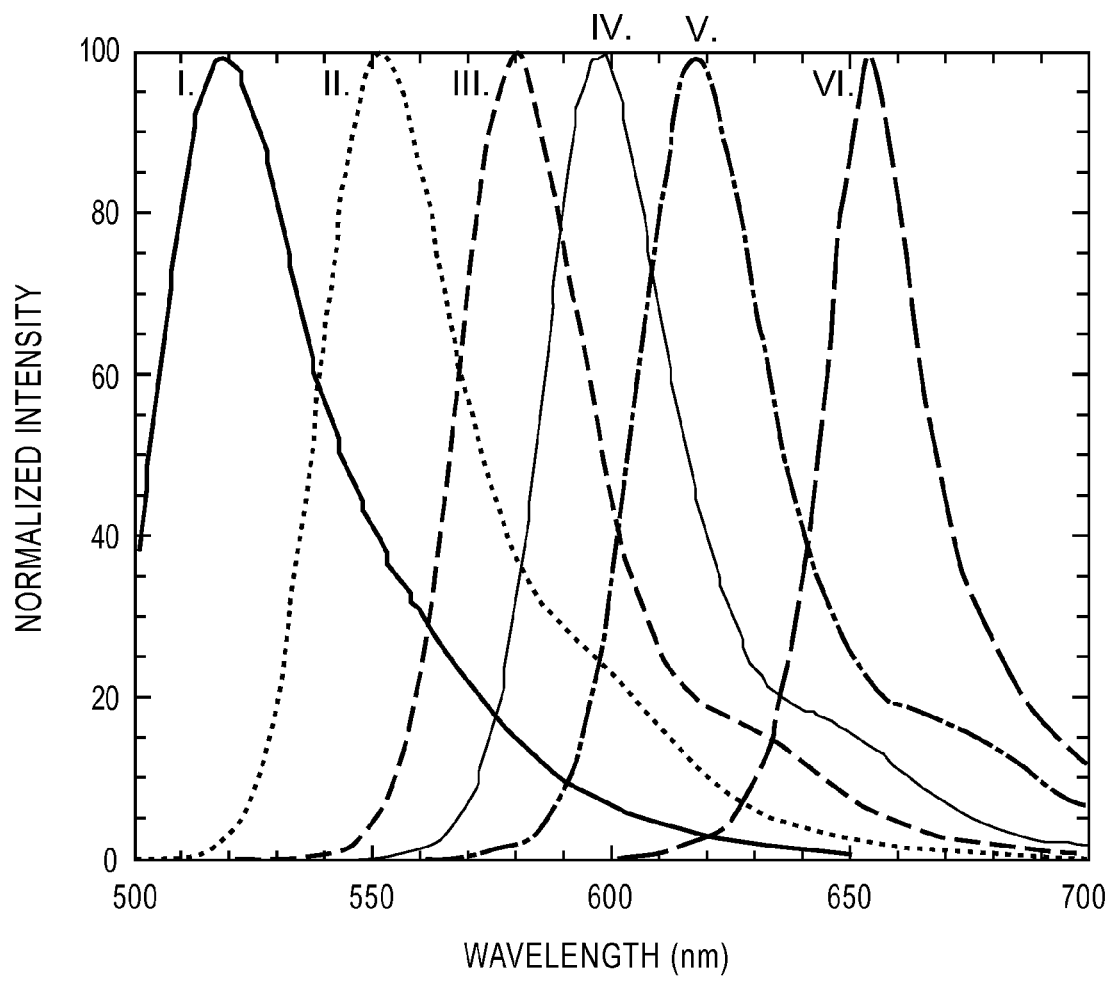
FIG. 15 is a graph showing the normalized fluorescence emission spectra of each dye of a set of six dyes according to various embodiments of the present teachings, wherein the set includes Sulfo-DDAO as a reference dye end five reporter dyes of shorter emission wavelengths.

FIG. 15 is a graph showing the normalized emission intensity of each dye of a set of six dyes according to venous embodiments of the present teachings, wherein the set includes Sulfo-DDAO as a passive reference dye and five reporter dyes of shorter wavelengths in various embodiments, and as shown in FIGS. 12-14, the reporter dyes can be selected so that the set is spectrally distinct and readily resolvability from other dyes of the set with respect to detection. The five reporter dyes shown are 6-FAM™, VIC®, ABY®, Dye 3.5, and JUN®, which have peak emissions of 518, 552, 583, 603, and 618 nm, respectively. Each dye is conjugated to an oligonucleotide, and the spectra are taken at 1 µM in Tris-EDTA buffer (1× stock concentration). The reference dye is Sulfo-DDAO is a free dye, and is not conjugated to an oligonucleotide. Other sets reporter dyes can be chosen from the many possibilities described herein and known in the art.

Figure 16:
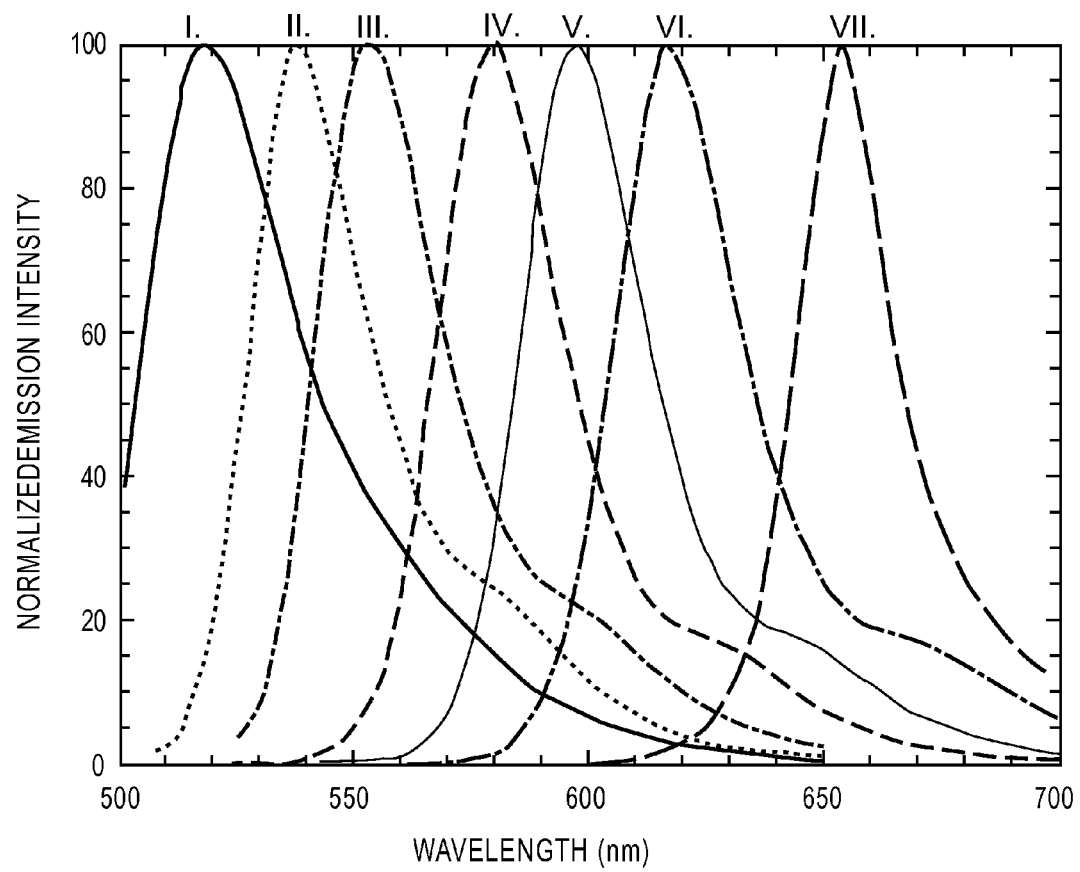
FIG. 16 is a graph showing the normalized fluorescence emission spectra of each dye of a set of seen dyes according to various embodiments of the present teachings, wherein the set includes Sulfo-DDAO as a reference dye and six reporter dyes of shorter emission wavelengths.

FIG. 16 is a graph showing the normalized emission intensity of each dye of a set of seven dyes according to various embodiments of the present teachings, wherein the set includes Sulfo-DDAO as a passive reference dye and six active days of shorter wavelengths. The reporter dyes can be selected so that the set is spectrally distinct and readily resolvability from other dyes of the set with respect to detection. The six reporter dyes shown are 6-FAM™, TET®, HEX®, ABY®, Dye 3.5, and JUN®, which have peak emissions of 518, 538, 553, 584, 603, and 618 nm, respectively. Each dye is conjugated to an oligonucleotide, and the spectra are taken at 1 μM in Tris-EDTA buffer (1× stock-concentration). The reference dye is Sulfo-DDAO is a free dye, and is not conjugated to an oligonucleotide. Other sets reporter dyes can be chosen from the many possibilities described herein and known in the art.

Figure 17:
FIG. 17 is a matrix showing an optimized use of Sulfo-DDAO as a reference dye to a four-reporter TAQMAN® Duplex SNP Genotyping experiment wherein about 98% of the reaction sets yielded good genotyping results.

FIG. 17 is a matrix showing the results of SNP genotyping of 12 different loci in corn using Sulfo-DDAO as a reference dye in a four-reporter TAQMAN® Duplex experiment. Two allele-specific probes for each locus are labeled with FAM™ and VIC® (a) or TED® and SID® (b) and assayed together. The genomic DNA and four probes were suspended in a multiplex PCR master mix in a 96 well plate and subjected to 40 cycles of PCR prior to measuring the end-point fluorescence signal in each well. In that experiment, about 98% of the reaction sets yielded good genotyping results. That is, for 98% of the assay combinations, two loci were able to be genotyped in the same assay without interference from the other. Only the two combinations shown in light gray yielded less than optimal results (10a/9b and 11a/9b). None of the reactions failed to amplify the targets, however. Accordingly, these results demonstrate that Sulfo-DDAO can be used as a reference dye in multiplexed systems, such as this four-reporter system.

Variations of kit components are contemplated in various embodiments of a kit according to the present teachings. In some embodiments of a kit, a probe is a labeled oligonucleotide, which comprises an oligonucleotide and a reporter dye. In some embodiments, the reporter dye is a fluorescent dye. In some embodiments, the reporter dye may be selected from the fluorescent dyes listed in Table 1. In some embodiments, the reference dye may be an ingredient in a master mix in a kit. In some embodiments, the reference dye and a master mix maybe be separate containers in a kit. In some embodiments, the reference dye and each of the at least one probes may be in separate containers in a kit. In some embodiments, the reference dye may be in a master mix, and the master mix and each of the at least one probes are in separate containers in a kit. In some embodiments, the reference dye, a master mix, and each of the at least one probes may be in separate containers in a kit. In some embodiments, the reference dye and at least one of the probes may be in the same container in the kit. In some embodiments, at least two of the probes may be in the same container, while the reference dye is in a separate container in the kit. In various embodiments, the kit components may be supplied lyophilized or suspended in a buffer solution. In some embodiments, the kit comprises instructions for using the reference dye and the probes. Such instructions, in some embodiments, may be instructions for carrying out an assay.

Reporter dyes that can be used in the present teachings are not limited to those discussed herein and can include a wide variety of different dyes, including, but not limited to, FRET dyes, non-FRET dyes, and combinations thereof. As noted above, in some embodiments, the reporter dyes are spectrally distinguishable from each other and from the reference dye. In some embodiments, the reporter dyes are distinguishable from each other and from the reference dye by their emission decay rates. The reporters can be chosen from the many possibilities discussed herein and in Table 1 above. The ability to use a stable reference dye with a set of six other dyes as shown in FIG. 16 is evidence that the Sulfo-DDAO reference dye of the present teachings can be useful in multiplexing assays that can detect, for example, but not limited by, at least six different analytes in the same assay. Different emission filter band passes, filter wheels, and other filtering and detection systems that can be used in such a method include those described herein and those that will become apparent to those of skill in the art given the present teachings.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. The teachings should not be read as limited to the described order or elements unless stated to that effect. It should be understood that various changes in form and detail may be made without departing from the scope of the present teachings, including the order and arrangement of disclosed method steps. Therefore, all embodiments that come within the scope and spirit of the present teachings and equivalents thereto are claimed.

What is claimed is:
1. A method comprising:
(a) contacting a sample which may comprise at least one target polynucleotide with at least one probe and a reference dye to form a mixture, wherein each of the at least one probes comprises a target-specific moiety, a reporter dye and a quencher dye, wherein each target-specific moiety is an oligonucleotide and is specific for a different target and each reporter dye is different from the other reporter dyes and is different from the reference dye, and wherein the reference dye has formula (I):

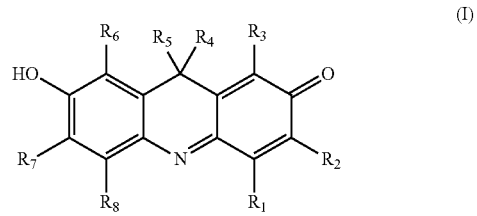

wherein:
each of $R_1$ to $R_3$ and $R_6$ to $R_8$ is independently —H, halogen, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, and substituted $C_1$-$C_6$ alkoxy, wherein R is $C_1$-$C_6$ alkyl, substituted $C_1$-$C_6$ alkyl, $C_1$-$C_6$ alkoxy, and substituted $C_1$-$C_6$ alkoxy;
$R_4$ and $R_5$ taken separately are selected from $C_1$-$C_6$ alkyl, and $C_1$-$C_6$ substituted alkyl, or $R_4$ and $R_5$ taken together are selected from $C_3$-$C_7$ cycloalkyl, $C_4$-$C_7$ unsaturated cycloalkyl, $C_3$-$C_7$ substituted cycloalkyl, or $C_4$-$C_7$ substituted unsaturated cycloalkyl;
(b) amplifying a target polynucleotide in the mixture to form an amplified mixture;
(c) measuring fluorescence emitted by the reference dye; and
(d) measuring fluorescence emitted by at least one reporter dye.

2. The method of claim 1, further comprising adjusting the measured fluorescence emitted by the at least one reporter dye based on the measured fluorescence emitted by the reference dye, to form an adjusted measurement.

3. The method of claim 1, wherein the method comprises:
irradiating the amplified mixture with a first excitation wavelength range;
detecting radiation emitted by at least a first reporter dye; and
detecting radiation emitted by at least a second reporter dye;
wherein the radiation emitted by each reporter dye can be measured in the presence of the other reporter dyes and the reference dye in the amplified mixture.

4. The method of claim 1, wherein $R_1$ is selected from hydrogen, halogen, methyl, and ethyl; $R_2$ and $R_3$ are each independently a halogen; $R_4$ and $R_5$ are each independently selected from methyl and ethyl; $R_6$ is selected from hydrogen, halogen, methyl, and ethyl; $R_7$ is selected from hydrogen, halogen, methyl, ethyl, and $SO_3H$; and $R_8$ is selected from hydrogen, halogen, methyl, and ethyl.

5. The method of claim 1, wherein $R_2$ and $R_3$ are each chlorine and $R_7$ is hydrogen or $SO_3H$.

6. The method of claim 1, wherein the reference dye is selected from:

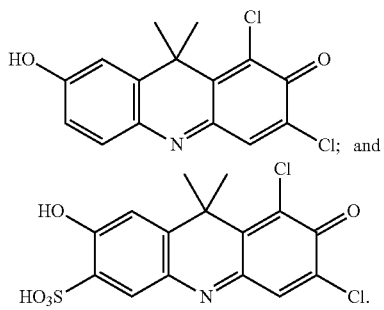

7. The method of claim 1, wherein the step of measuring the fluorescence emitted by the at least one reporter dye indicates the presence or absence of the at least one target polynucleotide.

8. The method of claim 1, wherein the mixture comprises more than one probe whereby multiple targets may be detected in a single sample region of a sample containment device.

9. The method of claim 2, wherein the amount of measured fluorescence emitted by the at least one reporter dye indicates the amount of the at least one target polynucleotide present in the sample.

10. The method of claim 1, wherein the mixture further comprises a protein selected from the group consisting of DNA polymerase, a ligase, a reverse transcriptase, a ribonuclease, a glycosylase, a single strand binding protein, a pyrophosphatase, an albumin, and a gelatin.

11. The method of claim 1, wherein the amplifying step comprises a PCR.

12. The method of claim 11, wherein the PCR degrades the at least one probe, separating the reporter dye from the quencher dye, thereby releasing fluorescence of the reporter dye.

13. The method of claim 1, wherein the amplifying step further comprises hybridizing the at least one probe with the at least one target polynucleotide, thereby separating the reporter dye and the quencher dye such that fluorescence is detectable from the reporter dye.

14. A method comprising:
(a) contacting a sample which may comprise at least one target polynucleotide with at least one probe and a reference dye to form a mixture, wherein each of the at least one probes comprises a target-specific moiety, a reporter dye and a quencher dye, wherein each target-specific moiety is an oligonucleotide and is specific for a different target and each reporter dye is different from the other reporter dyes and is different from the reference dye, and wherein the reference dye has formula:

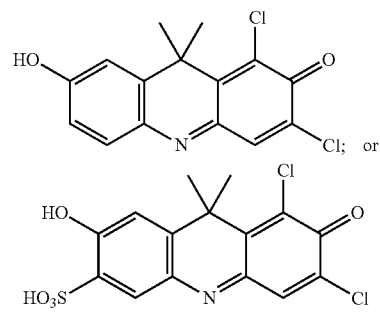

(b) amplifying a target polynucleotide in the mixture;
(c) measuring fluorescence emitted by the reference dye; and
(d) measuring fluorescence emitted by at least one reporter dye.

15. A method comprising:
(a) contacting a sample which may comprise at least one target polynucleotide with two to six probes and a reference dye to form a mixture, wherein each of the two to six probes comprises a target-specific moiety, a reporter dye and a quencher dye, wherein each target-specific moiety is an oligonucleotide and is specific for a different target and each reporter dye is different from the other reporter dyes and is different from the reference dye, and wherein the reference dye has formula (I):

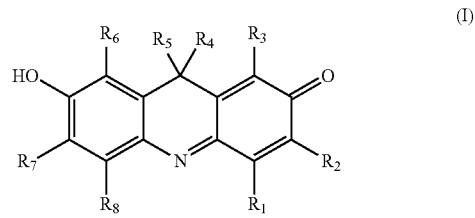

wherein:
each of $R_1$ to $R_3$ and $R_6$ to $R_8$ is independently —H, halogen, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, and substituted $C_1$-$C_6$ alkoxy, wherein R is $C_1$-$C_6$ alkyl, substituted $C_1$-$C_6$ alkyl, $C_1$-$C_6$ alkoxy, and substituted $C_1$-$C_6$ alkoxy;
$R_4$ and $R_5$ taken separately are selected from $C_1$-$C_6$ alkyl, and $C_1$-$C_6$ substituted alkyl, or $R_4$ and $R_5$ taken together are selected from $C_3$-$C_7$ cycloalkyl, $C_4$-$C_7$ unsaturated cycloalkyl, $C_3$-$C_7$ substituted cycloalkyl, or $C_4$-$C_7$ substituted unsaturated cycloalkyl;

(b) amplifying a target polynucleotide in a PCR, wherein at least one reporter dye separates from the respective quencher dye during the PCR, thereby releasing fluorescence of the at least one reporter dye;
(c) measuring fluorescence emitted by the reference dye; and
(d) measuring fluorescence emitted by the at least one reporter dye.

16. The method of claim 1, wherein the mixture comprises two to six probes.

\* \* \* \* \*